United States Patent
Johansson et al.

(10) Patent No.: US 10,942,022 B2
(45) Date of Patent: Mar. 9, 2021

(54) MANUAL CALIBRATION OF IMAGING SYSTEM

(71) Applicant: PHILIPS IMAGE GUIDED THERAPY CORPORATION, San Diego, CA (US)

(72) Inventors: Andreas Johansson, San Diego, CA (US); Jason Sproul, Watertown, MA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 0 days.

(21) Appl. No.: 14/107,861

(22) Filed: Dec. 16, 2013

(65) Prior Publication Data

US 2014/0176961 A1 Jun. 26, 2014

Related U.S. Application Data

(60) Provisional application No. 61/739,881, filed on Dec. 20, 2012.

(51) Int. Cl.
*G01B 9/02* (2006.01)
*A61B 5/00* (2006.01)
(Continued)

(52) U.S. Cl.
CPC ........ *G01B 9/02091* (2013.01); *A61B 5/0066* (2013.01); *A61B 5/0073* (2013.01);
(Continued)

(58) Field of Classification Search
None
See application file for complete search history.

(56) References Cited

U.S. PATENT DOCUMENTS 3,301,258 A  1/1967 Werner
3,617,880 A  11/1971 Cormack et al.
(Continued)

FOREIGN PATENT DOCUMENTS

EP  1041373 A2  10/2000
EP  01172637 A1  1/2002
(Continued)

OTHER PUBLICATIONS

Bell, Malcolm R., et al. "Validation of a new UNIX-based quantitative coronary angiographic system for the measurement of coronary artery lesions." Catheterization and cardiovascular diagnosis 40.1 (1997): 66-74.*

(Continued)

*Primary Examiner* — Vu Le
*Assistant Examiner* — Tracy Mangialaschi

(57) ABSTRACT

The invention generally relates to methods for manually calibrating imaging systems such as optical coherence tomography systems. In certain aspects, an imaging system displays an image showing a target and a reference item. A user looks at the image and indicates a point within the image near the reference item. A processor detects an actual location of the reference item within an area around the indicated point. The processor can use an expected location of the reference item with the detected actual location to calculate a calibration value and provide a calibrated image. In this way, a user can identify the actual location of the reference point and a processing algorithm can give precision to the actual location.

20 Claims, 16 Drawing Sheets

(51) Int. Cl.
*G01B 21/04* (2006.01)
*G06T 7/80* (2017.01)

(52) U.S. Cl.
CPC ..... *G01B 9/02072* (2013.04); *G01B 9/02089* (2013.01); *G01B 21/045* (2013.01); *G06T 7/80* (2017.01); *A61B 5/7475* (2013.01); *A61B 2560/0223* (2013.01); *G06T 2207/10101* (2013.01); *G06T 2207/20101* (2013.01); *G06T 2207/30101* (2013.01)

(56) References Cited

U.S. PATENT DOCUMENTS

| | | |
|---|---|---|
| 3,789,841 A | 2/1974 | Antoshkiw |
| 3,841,308 A | 10/1974 | Tate |
| 4,140,364 A | 2/1979 | Yamashita et al. |
| 4,274,423 A | 6/1981 | Mizuno et al. |
| 4,344,438 A | 8/1982 | Schultz |
| 4,398,791 A | 8/1983 | Dorsey |
| 4,432,370 A | 2/1984 | Hughes et al. |
| 4,552,554 A | 11/1985 | Gould et al. |
| 4,577,543 A | 3/1986 | Wilson |
| 4,676,980 A | 6/1987 | Segal et al. |
| 4,682,895 A | 7/1987 | Costello |
| 4,733,665 A | 3/1988 | Palmaz |
| 4,744,619 A | 5/1988 | Cameron |
| 4,762,129 A | 8/1988 | Bonzel |
| 4,766,386 A | 8/1988 | Oliver et al. |
| 4,771,774 A | 9/1988 | Simpson et al. |
| 4,794,931 A | 1/1989 | Yock |
| 4,800,886 A | 1/1989 | Nestor |
| 4,803,639 A | 2/1989 | Steele et al. |
| 4,816,567 A | 3/1989 | Cabilly et al. |
| 4,819,740 A | 4/1989 | Warrington |
| 4,821,731 A | 4/1989 | Martinelli et al. |
| 4,824,435 A | 4/1989 | Giesy et al. |
| 4,830,023 A | 5/1989 | de Toledo et al. |
| 4,834,093 A | 5/1989 | Littleford et al. |
| 4,841,977 A | 6/1989 | Griffith et al. |
| 4,864,578 A | 9/1989 | Proffitt et al. |
| 4,873,690 A | 10/1989 | Adams |
| 4,877,314 A | 10/1989 | Kanamori |
| 4,887,606 A | 12/1989 | Yock et al. |
| 4,917,085 A | 4/1990 | Smith |
| 4,917,097 A | 4/1990 | Proudian et al. |
| 4,928,693 A | 5/1990 | Goodin et al. |
| 4,932,413 A | 6/1990 | Shockey et al. |
| 4,932,419 A | 6/1990 | de Toledo |
| 4,948,229 A | 8/1990 | Soref |
| 4,951,677 A | 8/1990 | Crowley et al. |
| 4,969,742 A | 11/1990 | Falk et al. |
| 4,987,412 A | 1/1991 | Vaitekunas et al. |
| 4,993,412 A | 2/1991 | Murphy-Chutorian |
| 4,998,972 A | 3/1991 | Chin et al. |
| 5,000,185 A | 3/1991 | Yock |
| 5,024,234 A | 6/1991 | Leary et al. |
| 5,025,445 A | 6/1991 | Anderson et al. |
| 5,032,123 A | 7/1991 | Katz et al. |
| 5,037,169 A | 8/1991 | Chun |
| 5,039,193 A | 8/1991 | Snow et al. |
| 5,040,548 A | 8/1991 | Yock |
| 5,041,108 A | 8/1991 | Fox et al. |
| 5,054,492 A | 10/1991 | Scribner et al. |
| 5,065,010 A | 11/1991 | Knute |
| 5,065,769 A | 11/1991 | de Toledo |
| 5,085,221 A | 2/1992 | Ingebrigtsen et al. |
| 5,095,911 A | 3/1992 | Pomeranz |
| 5,100,424 A | 3/1992 | Jang et al. |
| 5,120,308 A | 6/1992 | Hess |
| 5,125,137 A | 6/1992 | Corl et al. |
| 5,135,486 A | 8/1992 | Eberle et al. |
| 5,135,516 A | 8/1992 | Sahatjian et al. |
| 5,155,439 A | 10/1992 | Holmbo et al. |
| 5,158,548 A | 10/1992 | Lau et al. |
| 5,163,445 A | 11/1992 | Christian et al. |
| 5,167,233 A | 12/1992 | Eberle et al. |
| 5,174,295 A | 12/1992 | Christian et al. |
| 5,176,141 A | 1/1993 | Bom et al. |
| 5,176,674 A | 1/1993 | Hofmann |
| 5,178,159 A | 1/1993 | Christian |
| 5,183,048 A | 2/1993 | Eberle |
| 5,188,632 A | 2/1993 | Goldenberg |
| 5,201,316 A | 4/1993 | Pomeranz et al. |
| 5,202,745 A | 4/1993 | Sorin et al. |
| 5,203,779 A | 4/1993 | Muller et al. |
| 5,220,922 A | 6/1993 | Barany |
| 5,224,953 A | 7/1993 | Morgentaler |
| 5,226,421 A | 7/1993 | Frisbie et al. |
| 5,240,003 A | 8/1993 | Lancee et al. |
| 5,240,437 A | 8/1993 | Christian |
| 5,242,460 A | 9/1993 | Klein et al. |
| 5,243,988 A | 9/1993 | Sieben et al. |
| 5,257,974 A | 11/1993 | Cox |
| 5,266,302 A | 11/1993 | Peyman et al. |
| 5,267,954 A | 12/1993 | Nita |
| 5,301,001 A | 4/1994 | Murphy et al. |
| 5,312,425 A | 5/1994 | Evans et al. |
| 5,313,949 A | 5/1994 | Yock |
| 5,313,957 A | 5/1994 | Little |
| 5,319,492 A | 6/1994 | Dorn et al. |
| 5,321,501 A | 6/1994 | Swanson et al. |
| 5,325,198 A | 6/1994 | Hartley et al. |
| 5,336,178 A | 8/1994 | Kaplan et al. |
| 5,346,689 A | 9/1994 | Peyman et al. |
| 5,348,017 A | 9/1994 | Thornton et al. |
| 5,348,481 A | 9/1994 | Ortiz |
| 5,353,798 A | 10/1994 | Sieben |
| 5,358,409 A | 10/1994 | Obara |
| 5,358,478 A | 10/1994 | Thompson et al. |
| 5,368,037 A | 11/1994 | Eberle et al. |
| 5,373,845 A | 12/1994 | Gardineer et al. |
| 5,373,849 A | 12/1994 | Maroney et al. |
| 5,375,602 A | 12/1994 | Lancee et al. |
| 5,377,682 A | 1/1995 | Ueno et al. |
| 5,383,853 A | 1/1995 | Jung et al. |
| 5,387,193 A | 2/1995 | Miraki |
| 5,396,328 A | 3/1995 | Jestel et al. |
| 5,397,355 A | 3/1995 | Marin et al. |
| 5,405,377 A | 4/1995 | Cragg |
| 5,411,016 A | 5/1995 | Kume et al. |
| 5,419,777 A | 5/1995 | Hofling |
| 5,421,338 A | 6/1995 | Crowley et al. |
| 5,423,806 A | 6/1995 | Dale et al. |
| 5,427,118 A | 6/1995 | Nita et al. |
| 5,431,673 A | 7/1995 | Summers et al. |
| 5,436,759 A | 7/1995 | Dijaili et al. |
| 5,439,139 A | 8/1995 | Brovelli |
| 5,443,457 A | 8/1995 | Ginn et al. |
| 5,453,575 A | 9/1995 | O'Donnell et al. |
| 5,456,693 A | 10/1995 | Conston et al. |
| 5,459,570 A | 10/1995 | Swanson et al. |
| 5,480,388 A | 1/1996 | Zadini et al. |
| 5,485,845 A | 1/1996 | Verdonk et al. |
| 5,492,125 A | 2/1996 | Kim et al. |
| 5,496,997 A | 3/1996 | Pope |
| 5,507,761 A | 4/1996 | Duer |
| 5,512,044 A | 4/1996 | Duer |
| 5,514,128 A | 5/1996 | Hillsman et al. |
| 5,529,674 A | 6/1996 | Hedgcoth |
| 5,541,730 A | 7/1996 | Chaney |
| 5,546,717 A | 8/1996 | Penczak et al. |
| 5,546,948 A | 8/1996 | Hamm et al. |
| 5,565,332 A | 10/1996 | Hoogenboom et al. |
| 5,573,520 A | 11/1996 | Schwartz et al. |
| 5,581,638 A | 12/1996 | Givens et al. |
| 5,586,054 A | 12/1996 | Jensen et al. |
| 5,592,939 A | 1/1997 | Martinelli |
| 5,596,079 A | 1/1997 | Smith et al. |
| 5,598,844 A | 2/1997 | Diaz et al. |
| 5,609,606 A | 3/1997 | O'Boyle |
| 5,630,806 A | 5/1997 | Inagaki et al. |
| 5,651,366 A | 7/1997 | Liang et al. |
| 5,660,180 A | 8/1997 | Malinowski et al. |
| 5,667,499 A | 9/1997 | Welch et al. |

(56) References Cited

U.S. PATENT DOCUMENTS

| | | |
|---|---|---|
| 5,667,521 A | 9/1997 | Keown |
| 5,672,877 A | 9/1997 | Liebig et al. |
| 5,674,232 A | 10/1997 | Halliburton |
| 5,693,015 A | 12/1997 | Walker et al. |
| 5,713,848 A | 2/1998 | Dubrul et al. |
| 5,745,634 A | 4/1998 | Garrett et al. |
| 5,771,895 A | 6/1998 | Slager |
| 5,779,731 A | 7/1998 | Leavitt |
| 5,780,958 A | 7/1998 | Strugach et al. |
| 5,798,521 A | 8/1998 | Froggatt |
| 5,800,450 A | 9/1998 | Lary et al. |
| 5,803,083 A | 9/1998 | Buck et al. |
| 5,814,061 A | 9/1998 | Osborne et al. |
| 5,817,025 A | 10/1998 | Alekseev et al. |
| 5,820,594 A | 10/1998 | Fontirroche et al. |
| 5,824,520 A | 10/1998 | Mulligan-Kehoe |
| 5,827,313 A | 10/1998 | Ream |
| 5,830,222 A | 11/1998 | Makower |
| 5,848,121 A | 12/1998 | Gupta et al. |
| 5,851,464 A | 12/1998 | Davila et al. |
| 5,857,974 A | 1/1999 | Eberle et al. |
| 5,872,829 A | 2/1999 | Wischmann et al. |
| 5,873,835 A | 2/1999 | Hastings et al. |
| 5,882,722 A | 3/1999 | Kydd |
| 5,912,764 A | 6/1999 | Togino |
| 5,916,194 A | 6/1999 | Jacobsen et al. |
| 5,921,931 A | 7/1999 | O'Donnell et al. |
| 5,925,055 A | 7/1999 | Adrian et al. |
| 5,949,929 A | 9/1999 | Hamm |
| 5,951,586 A | 9/1999 | Berg et al. |
| 5,974,521 A | 10/1999 | Akerib |
| 5,976,120 A | 11/1999 | Chow et al. |
| 5,978,391 A | 11/1999 | Das et al. |
| 5,997,523 A | 12/1999 | Jang |
| 6,021,240 A | 2/2000 | Murphy et al. |
| 6,022,319 A | 2/2000 | Willard et al. |
| 6,031,071 A | 2/2000 | Mandeville et al. |
| 6,036,889 A | 3/2000 | Kydd |
| 6,043,883 A | 3/2000 | Leckel et al. |
| 6,050,949 A | 4/2000 | White et al. |
| 6,059,738 A | 5/2000 | Stoltze et al. |
| 6,068,638 A | 5/2000 | Makower |
| 6,074,362 A | 6/2000 | Jang et al. |
| 6,078,831 A | 6/2000 | Belef et al. |
| 6,080,109 A | 6/2000 | Baker et al. |
| 6,091,496 A | 7/2000 | Hill |
| 6,094,591 A | 7/2000 | Foltz et al. |
| 6,095,976 A | 8/2000 | Nachtomy et al. |
| 6,097,755 A | 8/2000 | Guenther, Jr. et al. |
| 6,099,471 A | 8/2000 | Torp et al. |
| 6,099,549 A | 8/2000 | Bosma et al. |
| 6,102,938 A | 8/2000 | Evans et al. |
| 6,106,476 A | 8/2000 | Corl et al. |
| 6,120,445 A | 9/2000 | Grunwald |
| 6,123,673 A | 9/2000 | Eberle et al. |
| 6,134,003 A | 10/2000 | Tearney et al. |
| 6,139,510 A | 10/2000 | Palermo |
| 6,141,089 A | 10/2000 | Thoma et al. |
| 6,146,328 A | 11/2000 | Chiao et al. |
| 6,148,095 A | 11/2000 | Prause et al. |
| 6,151,433 A | 11/2000 | Dower et al. |
| 6,152,877 A | 11/2000 | Masters |
| 6,152,878 A | 11/2000 | Nachtomy et al. |
| 6,159,225 A | 12/2000 | Makower |
| 6,165,127 A | 12/2000 | Crowley |
| 6,176,842 B1 | 1/2001 | Tachibana et al. |
| 6,179,809 B1 | 1/2001 | Khairkhahan et al. |
| 6,186,949 B1 | 2/2001 | Hatfield et al. |
| 6,190,353 B1 | 2/2001 | Makower et al. |
| 6,200,266 B1 | 3/2001 | Shokrollahi et al. |
| 6,200,268 B1 | 3/2001 | Vince et al. |
| 6,203,537 B1 | 3/2001 | Adrian |
| 6,208,415 B1 | 3/2001 | De Boer et al. |
| 6,210,332 B1 | 4/2001 | Chiao et al. |
| 6,210,339 B1 | 4/2001 | Kiepen et al. |
| 6,212,308 B1 | 4/2001 | Donald |
| 6,231,518 B1 | 5/2001 | Grabek et al. |
| 6,245,066 B1 | 6/2001 | Morgan et al. |
| 6,249,076 B1 | 6/2001 | Madden et al. |
| 6,254,543 B1 | 7/2001 | Grunwald et al. |
| 6,256,090 B1 | 7/2001 | Chen et al. |
| 6,258,052 B1 | 7/2001 | Milo |
| 6,261,246 B1 | 7/2001 | Pantages et al. |
| 6,275,628 B1 | 8/2001 | Jones et al. |
| 6,283,921 B1 | 9/2001 | Nix et al. |
| 6,283,951 B1 | 9/2001 | Flaherty et al. |
| 6,295,308 B1 | 9/2001 | Zah |
| 6,299,622 B1 | 10/2001 | Snow et al. |
| 6,312,384 B1 | 11/2001 | Chiao |
| 6,325,797 B1 | 12/2001 | Stewart et al. |
| 6,328,696 B1 | 12/2001 | Fraser |
| 6,343,168 B1 | 1/2002 | Murphy et al. |
| 6,343,178 B1 | 1/2002 | Burns et al. |
| 6,350,240 B1 | 2/2002 | Song et al. |
| 6,364,841 B1 | 4/2002 | White et al. |
| 6,366,722 B1 | 4/2002 | Murphy et al. |
| 6,367,984 B1 | 4/2002 | Stephenson et al. |
| 6,373,970 B1 | 4/2002 | Dong et al. |
| 6,375,615 B1 | 4/2002 | Flaherty et al. |
| 6,375,618 B1 | 4/2002 | Chiao et al. |
| 6,375,628 B1 | 4/2002 | Zadno-Azizi et al. |
| 6,376,830 B1 | 4/2002 | Froggatt et al. |
| 6,379,352 B1 | 4/2002 | Reynolds et al. |
| 6,381,350 B1 | 4/2002 | Klingensmith et al. |
| 6,387,124 B1 | 5/2002 | Buscemi et al. |
| 6,396,976 B1 | 5/2002 | Little et al. |
| 6,398,792 B1 | 6/2002 | O'Connor |
| 6,417,948 B1 | 7/2002 | Chowdhury et al. |
| 6,419,644 B1 | 7/2002 | White et al. |
| 6,421,164 B2 | 7/2002 | Tearney et al. |
| 6,423,012 B1 | 7/2002 | Kato et al. |
| 6,426,796 B1 | 7/2002 | Pulliam et al. |
| 6,428,041 B1 | 8/2002 | Wohllebe et al. |
| 6,428,498 B2 | 8/2002 | Uflacker |
| 6,429,421 B1 | 8/2002 | Meller et al. |
| 6,440,077 B1 | 8/2002 | Jung et al. |
| 6,443,903 B1 | 9/2002 | White et al. |
| 6,450,964 B1 | 9/2002 | Webler |
| 6,457,365 B1 | 10/2002 | Stephens et al. |
| 6,459,844 B1 | 10/2002 | Pan |
| 6,468,290 B1 | 10/2002 | Weldon et al. |
| 6,475,149 B1 | 11/2002 | Sumanaweera |
| 6,480,285 B1 | 11/2002 | Hill |
| 6,491,631 B2 | 12/2002 | Chiao et al. |
| 6,491,636 B2 | 12/2002 | Chenal et al. |
| 6,501,551 B1 | 12/2002 | Tearney et al. |
| 6,504,286 B1 | 1/2003 | Porat et al. |
| 6,508,824 B1 | 1/2003 | Flaherty et al. |
| 6,514,237 B1 | 2/2003 | Maseda |
| 6,520,269 B2 | 2/2003 | Geiger et al. |
| 6,520,677 B2 | 2/2003 | Iizuka |
| 6,535,764 B2 | 3/2003 | Imran et al. |
| 6,538,778 B1 | 3/2003 | Leckel et al. |
| 6,544,217 B1 | 4/2003 | Gulachenski |
| 6,544,230 B1 | 4/2003 | Flaherty et al. |
| 6,545,760 B1 | 4/2003 | Froggatt et al. |
| 6,546,272 B1 | 4/2003 | MacKinnon et al. |
| 6,551,250 B2 | 4/2003 | Khalil |
| 6,566,648 B1 | 5/2003 | Froggatt |
| 6,570,894 B2 | 5/2003 | Anderson |
| 6,572,555 B2 | 6/2003 | White et al. |
| 6,579,311 B1 | 6/2003 | Makower |
| 6,584,335 B1 | 6/2003 | Haar et al. |
| 6,592,612 B1 | 7/2003 | Samson et al. |
| 6,594,448 B2 | 7/2003 | Herman et al. |
| 6,602,241 B2 | 8/2003 | Makower et al. |
| 6,611,322 B1 | 8/2003 | Nakayama et al. |
| 6,611,720 B2 | 8/2003 | Hata et al. |
| 6,612,992 B1 | 9/2003 | Hossack et al. |
| 6,615,062 B2 | 9/2003 | Ryan et al. |
| 6,615,072 B1 | 9/2003 | Izatt et al. |
| 6,621,562 B2 | 9/2003 | Durston |
| 6,631,284 B2 | 10/2003 | Nutt et al. |
| 6,638,227 B2 | 10/2003 | Bae |

(56) References Cited

U.S. PATENT DOCUMENTS

| | | |
|---|---|---|
| 6,645,152 B1 | 11/2003 | Jung et al. |
| 6,646,745 B2 | 11/2003 | Verma et al. |
| 6,655,386 B1 | 12/2003 | Makower et al. |
| 6,659,957 B1 | 12/2003 | Vardi et al. |
| 6,660,024 B1 | 12/2003 | Flaherty et al. |
| 6,663,565 B2 | 12/2003 | Kawagishi et al. |
| 6,665,456 B2 | 12/2003 | Dave et al. |
| 6,669,716 B1 | 12/2003 | Gilson et al. |
| 6,671,055 B1 | 12/2003 | Wavering et al. |
| 6,673,015 B1 | 1/2004 | Glover et al. |
| 6,673,064 B1 | 1/2004 | Rentrop |
| 6,685,648 B2 | 2/2004 | Flaherty et al. |
| 6,689,056 B1 | 2/2004 | Kilcoyne et al. |
| 6,689,144 B2 | 2/2004 | Gerberding |
| 6,696,173 B1 | 2/2004 | Naundorf et al. |
| 6,701,044 B2 | 3/2004 | Arbore et al. |
| 6,701,176 B1 | 3/2004 | Halperin et al. |
| 6,709,444 B1 | 3/2004 | Makower |
| 6,712,836 B1 | 3/2004 | Berg et al. |
| 6,714,703 B2 | 3/2004 | Lee et al. |
| 6,719,717 B1 | 4/2004 | Johnson et al. |
| 6,725,073 B1 | 4/2004 | Motamedi et al. |
| 6,726,677 B1 | 4/2004 | Flaherty et al. |
| 6,730,107 B2 | 5/2004 | Kelley et al. |
| 6,733,474 B2 | 5/2004 | Kusleika |
| 6,738,144 B1 | 5/2004 | Dogariu |
| 6,740,113 B2 | 5/2004 | Vrba |
| 6,746,464 B1 | 6/2004 | Makower |
| 6,780,157 B2 | 8/2004 | Stephens et al. |
| 6,795,188 B2 | 9/2004 | Ruck et al. |
| 6,795,196 B2 | 9/2004 | Funakawa |
| 6,798,522 B2 | 9/2004 | Stolte et al. |
| 6,822,798 B2 | 11/2004 | Wu et al. |
| 6,830,559 B2 | 12/2004 | Schock |
| 6,832,024 B2 | 12/2004 | Gerstenberger et al. |
| 6,842,639 B1 | 1/2005 | Winston et al. |
| 6,847,449 B2 | 1/2005 | Bashkansky et al. |
| 6,855,115 B2 | 2/2005 | Fonseca et al. |
| 6,856,138 B2 | 2/2005 | Bohley |
| 6,856,400 B1 | 2/2005 | Froggatt |
| 6,856,472 B2 | 2/2005 | Herman et al. |
| 6,860,867 B2 | 3/2005 | Seward et al. |
| 6,866,670 B2 | 3/2005 | Rabiner et al. |
| 6,878,113 B2 | 4/2005 | Miwa et al. |
| 6,886,411 B2 | 5/2005 | Kjellman et al. |
| 6,891,984 B2 | 5/2005 | Petersen et al. |
| 6,895,106 B2 | 5/2005 | Wang et al. |
| 6,898,337 B2 | 5/2005 | Averett et al. |
| 6,900,897 B2 | 5/2005 | Froggatt |
| 6,912,051 B2 | 6/2005 | Jensen |
| 6,916,329 B1 | 7/2005 | Zhao |
| 6,922,498 B2 | 7/2005 | Shah |
| 6,937,346 B2 | 8/2005 | Nebendahl et al. |
| 6,937,696 B1 | 8/2005 | Mostafavi |
| 6,943,939 B1 | 9/2005 | DiJaili et al. |
| 6,947,147 B2 | 9/2005 | Motamedi et al. |
| 6,947,787 B2 | 9/2005 | Webler |
| 6,949,094 B2 | 9/2005 | Yaron |
| 6,952,603 B2 | 10/2005 | Gerber et al. |
| 6,954,737 B2 | 10/2005 | Kalantar et al. |
| 6,958,042 B2 | 10/2005 | Honda |
| 6,961,123 B1 | 11/2005 | Wang et al. |
| 6,966,891 B2 | 11/2005 | Ookubo et al. |
| 6,969,293 B2 | 11/2005 | Thai |
| 6,969,395 B2 | 11/2005 | Eskuri |
| 6,985,234 B2 | 1/2006 | Anderson |
| 7,004,963 B2 | 2/2006 | Wang et al. |
| 7,006,231 B2 | 2/2006 | Ostrovsky et al. |
| 7,010,458 B2 | 3/2006 | Wilt |
| 7,024,025 B2 | 4/2006 | Sathyanarayana |
| 7,027,211 B1 | 4/2006 | Ruffa |
| 7,027,743 B1 | 4/2006 | Tucker et al. |
| 7,033,347 B2 | 4/2006 | Appling |
| 7,035,484 B2 | 4/2006 | Silberberg et al. |
| 7,037,269 B2 | 5/2006 | Nix et al. |
| 7,042,573 B2 | 5/2006 | Froggatt |
| 7,044,915 B2 | 5/2006 | White et al. |
| 7,044,964 B2 | 5/2006 | Jang et al. |
| 7,048,711 B2 | 5/2006 | Rosenman et al. |
| 7,049,306 B2 | 5/2006 | Konradi et al. |
| 7,058,239 B2 | 6/2006 | Singh et al. |
| 7,060,033 B2 | 6/2006 | White et al. |
| 7,060,421 B2 | 6/2006 | Naundorf et al. |
| 7,063,679 B2 | 6/2006 | Maguire et al. |
| 7,068,852 B2 | 6/2006 | Braica |
| 7,074,188 B2 | 7/2006 | Nair et al. |
| 7,095,493 B2 | 8/2006 | Harres |
| 7,110,119 B2 | 9/2006 | Maestle |
| 7,113,875 B2 | 9/2006 | Terashima et al. |
| 7,123,777 B2 | 10/2006 | Rondinelli et al. |
| 7,130,054 B2 | 10/2006 | Ostrovsky et al. |
| 7,139,440 B2 | 11/2006 | Rondinelli et al. |
| 7,153,299 B1 | 12/2006 | Tu et al. |
| 7,171,078 B2 | 1/2007 | Sasaki et al. |
| 7,175,597 B2 | 2/2007 | Vince et al. |
| 7,177,491 B2 | 2/2007 | Dave et al. |
| 7,190,464 B2 | 3/2007 | Alphonse |
| 7,215,802 B2 | 5/2007 | Klingensmith et al. |
| 7,218,811 B2 | 5/2007 | Shigenaga et al. |
| 7,236,812 B1 | 6/2007 | Ballerstadt et al. |
| 7,245,125 B2 | 7/2007 | Harer et al. |
| 7,245,789 B2 | 7/2007 | Bates et al. |
| 7,249,357 B2 | 7/2007 | Landman et al. |
| 7,291,146 B2 | 11/2007 | Steinke et al. |
| 7,292,715 B2 | 11/2007 | Furnish |
| 7,292,885 B2 | 11/2007 | Scott et al. |
| 7,294,124 B2 | 11/2007 | Eidenschink |
| 7,300,460 B2 | 11/2007 | Levine et al. |
| 7,335,161 B2 | 2/2008 | Von Arx et al. |
| 7,337,079 B2 | 2/2008 | Park et al. |
| 7,355,716 B2 | 4/2008 | de Boer et al. |
| 7,356,367 B2 | 4/2008 | Liang et al. |
| 7,358,921 B2 | 4/2008 | Snyder et al. |
| 7,359,062 B2 | 4/2008 | Chen et al. |
| 7,359,554 B2 | 4/2008 | Klingensmith et al. |
| 7,363,927 B2 | 4/2008 | Ravikumar |
| 7,366,376 B2 | 4/2008 | Shishkov et al. |
| 7,382,949 B2 | 6/2008 | Bouma et al. |
| 7,387,636 B2 | 6/2008 | Cohn et al. |
| 7,391,520 B2 | 6/2008 | Zhou et al. |
| 7,397,935 B2 | 7/2008 | Kimmel et al. |
| 7,399,095 B2 | 7/2008 | Rondinelli |
| 7,408,648 B2 | 8/2008 | Kleen et al. |
| 7,414,779 B2 | 8/2008 | Huber et al. |
| 7,440,087 B2 | 10/2008 | Froggatt et al. |
| 7,447,388 B2 | 11/2008 | Bates et al. |
| 7,449,821 B2 | 11/2008 | Dausch |
| 7,450,165 B2 | 11/2008 | Ahiska |
| RE40,608 E | 12/2008 | Glover et al. |
| 7,458,967 B2 | 12/2008 | Appling et al. |
| 7,463,362 B2 | 12/2008 | Lasker et al. |
| 7,463,759 B2 | 12/2008 | Klingensmith et al. |
| 7,491,226 B2 | 2/2009 | Palmaz et al. |
| 7,515,276 B2 | 4/2009 | Froggatt et al. |
| 7,527,594 B2 | 5/2009 | Vardi et al. |
| 7,534,251 B2 | 5/2009 | WasDyke |
| 7,535,797 B2 | 5/2009 | Peng et al. |
| 7,547,304 B2 | 6/2009 | Johnson |
| 7,564,949 B2 | 7/2009 | Sattler et al. |
| 7,577,471 B2 | 8/2009 | Camus et al. |
| 7,583,857 B2 | 9/2009 | Xu et al. |
| 7,603,165 B2 | 10/2009 | Townsend et al. |
| 7,612,773 B2 | 11/2009 | Magnin et al. |
| 7,633,627 B2 | 12/2009 | Choma et al. |
| 7,645,229 B2 | 1/2010 | Armstrong |
| 7,658,715 B2 | 2/2010 | Park et al. |
| 7,660,452 B2 | 2/2010 | Zwirn et al. |
| 7,660,492 B2 | 2/2010 | Bates et al. |
| 7,666,204 B2 | 2/2010 | Thornton et al. |
| 7,672,790 B2 | 3/2010 | McGraw et al. |
| 7,680,247 B2 | 3/2010 | Atzinger et al. |
| 7,684,991 B2 | 3/2010 | Stohr et al. |
| 7,711,413 B2 | 5/2010 | Feldman et al. |
| 7,720,322 B2 | 5/2010 | Prisco |

(56) References Cited

U.S. PATENT DOCUMENTS

| | | |
|---|---|---|
| 7,728,986 B2 | 6/2010 | Lasker et al. |
| 7,734,009 B2 | 6/2010 | Brunner et al. |
| 7,736,317 B2 | 6/2010 | Stephens et al. |
| 7,742,795 B2 | 6/2010 | Stone et al. |
| 7,743,189 B2 | 6/2010 | Brown et al. |
| 7,762,954 B2 | 7/2010 | Nix et al. |
| 7,766,896 B2 | 8/2010 | Kornkven Volk et al. |
| 7,773,792 B2 | 8/2010 | Kimmel et al. |
| 7,775,981 B1 | 8/2010 | Guracar et al. |
| 7,777,399 B2 | 8/2010 | Eidenschink et al. |
| 7,781,724 B2 | 8/2010 | Childers et al. |
| 7,783,337 B2 | 8/2010 | Feldman et al. |
| 7,787,127 B2 | 8/2010 | Galle et al. |
| 7,792,342 B2 | 9/2010 | Barbu et al. |
| 7,801,343 B2 | 9/2010 | Unal et al. |
| 7,801,590 B2 | 9/2010 | Feldman et al. |
| 7,813,609 B2 | 10/2010 | Petersen et al. |
| 7,831,081 B2 | 11/2010 | Li |
| 7,846,101 B2 | 12/2010 | Eberle et al. |
| 7,853,104 B2 | 12/2010 | Oota et al. |
| 7,853,316 B2 | 12/2010 | Milner et al. |
| 7,860,555 B2 | 12/2010 | Saadat |
| 7,862,508 B2 | 1/2011 | Davies et al. |
| 7,872,759 B2 | 1/2011 | Tearney et al. |
| 7,880,868 B2 | 2/2011 | Aoki |
| 7,881,763 B2 | 2/2011 | Brauker et al. |
| 7,909,844 B2 | 3/2011 | Alkhatib et al. |
| 7,921,854 B2 | 4/2011 | Hennings et al. |
| 7,927,784 B2 | 4/2011 | Simpson |
| 7,929,148 B2 | 4/2011 | Kemp |
| 7,930,014 B2 | 4/2011 | Huennekens et al. |
| 7,930,104 B2 | 4/2011 | Baker et al. |
| 7,936,462 B2 | 5/2011 | Jiang et al. |
| 7,942,852 B2 | 5/2011 | Mas et al. |
| 7,947,012 B2 | 5/2011 | Spurchise et al. |
| 7,951,186 B2 | 5/2011 | Eidenschink et al. |
| 7,952,719 B2 | 5/2011 | Brennan, III |
| 7,972,353 B2 | 7/2011 | Hendriksen et al. |
| 7,976,492 B2 | 7/2011 | Brauker et al. |
| 7,977,950 B2 | 7/2011 | Maslen |
| 7,978,916 B2 | 7/2011 | Klingensmith et al. |
| 7,981,041 B2 | 7/2011 | McGahan |
| 7,981,151 B2 | 7/2011 | Rowe |
| 7,983,737 B2 | 7/2011 | Feldman et al. |
| 7,993,333 B2 | 8/2011 | Oral et al. |
| 7,995,210 B2 | 8/2011 | Tearney et al. |
| 7,996,060 B2 | 8/2011 | Trofimov et al. |
| 7,999,938 B2 | 8/2011 | Wang |
| 8,021,377 B2 | 9/2011 | Eskuri |
| 8,021,420 B2 | 9/2011 | Dolan |
| 8,036,732 B2 | 10/2011 | Milner |
| 8,040,586 B2 | 10/2011 | Smith et al. |
| 8,047,996 B2 | 11/2011 | Goodnow et al. |
| 8,049,900 B2 | 11/2011 | Kemp et al. |
| 8,050,478 B2 | 11/2011 | Li et al. |
| 8,050,523 B2 | 11/2011 | Younge et al. |
| 8,052,605 B2 | 11/2011 | Muller et al. |
| 8,057,394 B2 | 11/2011 | Dala-Krishna |
| 8,059,923 B2 | 11/2011 | Bates et al. |
| 8,070,800 B2 | 12/2011 | Lock et al. |
| 8,080,800 B2 | 12/2011 | Hoctor et al. |
| 8,088,102 B2 | 1/2012 | Adams et al. |
| 8,100,838 B2 | 1/2012 | Wright et al. |
| 8,104,479 B2 | 1/2012 | Glynn et al. |
| 8,108,030 B2 | 1/2012 | Castella et al. |
| 8,114,102 B2 | 2/2012 | Galdonik et al. |
| 8,116,605 B2 | 2/2012 | Petersen et al. |
| 8,125,648 B2 | 2/2012 | Milner et al. |
| 8,126,239 B2 | 2/2012 | Sun et al. |
| 8,133,199 B2 | 3/2012 | Weber et al. |
| 8,133,269 B2 | 3/2012 | Flechsenhar et al. |
| 8,140,708 B2 | 3/2012 | Zaharia et al. |
| 8,148,877 B2 | 4/2012 | Jiang et al. |
| 8,167,932 B2 | 5/2012 | Bourang et al. |
| 8,172,757 B2 | 5/2012 | Jaffe et al. |
| 8,177,809 B2 | 5/2012 | Mavani et al. |
| 8,187,191 B2 | 5/2012 | Hancock et al. |
| 8,187,267 B2 | 5/2012 | Pappone et al. |
| 8,187,830 B2 | 5/2012 | Hu et al. |
| 8,199,218 B2 | 6/2012 | Lee et al. |
| 8,206,429 B2 | 6/2012 | Gregorich et al. |
| 8,208,995 B2 | 6/2012 | Tearney et al. |
| 8,222,906 B2 | 7/2012 | Wyar et al. |
| 8,233,681 B2 | 7/2012 | Aylward et al. |
| 8,233,718 B2 | 7/2012 | Klingensmith et al. |
| 8,238,624 B2 | 8/2012 | Doi et al. |
| 8,239,938 B2 | 8/2012 | Simeral et al. |
| 8,277,386 B2 | 10/2012 | Ahmed et al. |
| 8,280,470 B2 | 10/2012 | Milner et al. |
| 8,289,284 B2 | 10/2012 | Glynn et al. |
| 8,289,522 B2 | 10/2012 | Tearney et al. |
| 8,298,147 B2 | 10/2012 | Huennekens et al. |
| 8,298,149 B2 | 10/2012 | Hastings et al. |
| 8,301,000 B2 | 10/2012 | Sillard et al. |
| 8,309,428 B2 | 11/2012 | Lemmerhirt et al. |
| 8,317,713 B2 | 11/2012 | Davies et al. |
| 8,323,201 B2 | 12/2012 | Towfiq et al. |
| 8,329,053 B2 | 12/2012 | Martin et al. |
| 8,336,643 B2 | 12/2012 | Harleman |
| 8,349,000 B2 | 1/2013 | Schreck |
| 8,353,945 B2 | 1/2013 | Andreas et al. |
| 8,353,954 B2 | 1/2013 | Cai et al. |
| 8,357,981 B2 | 1/2013 | Martin et al. |
| 8,361,097 B2 | 1/2013 | Patel et al. |
| 8,386,560 B2 | 2/2013 | Ma et al. |
| 8,398,591 B2 | 3/2013 | Mas et al. |
| 8,412,312 B2 | 4/2013 | Judell et al. |
| 8,417,491 B2 | 4/2013 | Trovato et al. |
| 8,449,465 B2 | 5/2013 | Nair et al. |
| 8,454,685 B2 | 6/2013 | Hariton et al. |
| 8,454,686 B2 | 6/2013 | Alkhatib |
| 8,475,522 B2 | 7/2013 | Jimenez et al. |
| 8,478,384 B2 | 7/2013 | Schmitt et al. |
| 8,486,062 B2 | 7/2013 | Belhe et al. |
| 8,486,063 B2 | 7/2013 | Werneth et al. |
| 8,491,567 B2 | 7/2013 | Magnin et al. |
| 8,500,798 B2 | 8/2013 | Rowe et al. |
| 8,550,911 B2 | 10/2013 | Sylla |
| 8,594,757 B2 | 11/2013 | Boppart et al. |
| 8,597,349 B2 | 12/2013 | Alkhatib |
| 8,600,477 B2 | 12/2013 | Beyar et al. |
| 8,600,917 B1 | 12/2013 | Schimert et al. |
| 8,601,056 B2 | 12/2013 | Lauwers et al. |
| 8,620,055 B2 | 12/2013 | Barratt et al. |
| 8,644,910 B2 | 2/2014 | Rousso et al. |
| 2001/0007940 A1 | 7/2001 | Tu et al. |
| 2001/0029337 A1 | 10/2001 | Pantages et al. |
| 2001/0037073 A1 | 11/2001 | White et al. |
| 2001/0046345 A1 | 11/2001 | Snyder et al. |
| 2001/0049548 A1 | 12/2001 | Vardi et al. |
| 2002/0034276 A1 | 3/2002 | Hu et al. |
| 2002/0041723 A1 | 4/2002 | Ronnekleiv et al. |
| 2002/0069676 A1 | 6/2002 | Kopp et al. |
| 2002/0089335 A1 | 7/2002 | Williams |
| 2002/0099289 A1 | 7/2002 | Crowley |
| 2002/0163646 A1 | 11/2002 | Anderson |
| 2002/0186818 A1 | 12/2002 | Arnaud et al. |
| 2002/0196446 A1 | 12/2002 | Roth et al. |
| 2002/0197456 A1 | 12/2002 | Pope |
| 2003/0004412 A1 | 1/2003 | Izatt et al. |
| 2003/0016604 A1 | 1/2003 | Hanes |
| 2003/0018273 A1 | 1/2003 | Corl et al. |
| 2003/0023153 A1 | 1/2003 | Izatt et al. |
| 2003/0032886 A1 | 2/2003 | Dgany et al. |
| 2003/0050871 A1 | 3/2003 | Broughton |
| 2003/0065371 A1 | 4/2003 | Satake |
| 2003/0069723 A1 | 4/2003 | Hegde |
| 2003/0077043 A1 | 4/2003 | Hamm et al. |
| 2003/0085635 A1 | 5/2003 | Davidsen |
| 2003/0090753 A1 | 5/2003 | Takeyama et al. |
| 2003/0092995 A1 | 5/2003 | Thompson |
| 2003/0093059 A1 | 5/2003 | Griffin et al. |
| 2003/0103212 A1 | 6/2003 | Westphal et al. |
| 2003/0152259 A1 | 8/2003 | Belykh et al. |

(56) References Cited

U.S. PATENT DOCUMENTS

| | | |
|---|---|---|
| 2003/0181802 A1 | 9/2003 | Ogawa |
| 2003/0187369 A1 | 10/2003 | Lewis et al. |
| 2003/0194165 A1 | 10/2003 | Silberberg et al. |
| 2003/0195419 A1 | 10/2003 | Harada |
| 2003/0208116 A1 | 11/2003 | Liang et al. |
| 2003/0212491 A1 | 11/2003 | Mitchell et al. |
| 2003/0219202 A1 | 11/2003 | Loeb et al. |
| 2003/0220749 A1 | 11/2003 | Chen et al. |
| 2003/0228039 A1 | 12/2003 | Green |
| 2004/0015065 A1 | 1/2004 | Panescu et al. |
| 2004/0023317 A1 | 2/2004 | Motamedi et al. |
| 2004/0028333 A1 | 2/2004 | Lomas |
| 2004/0037742 A1 | 2/2004 | Jen et al. |
| 2004/0042066 A1 | 3/2004 | Kinoshita et al. |
| 2004/0054287 A1 | 3/2004 | Stephens |
| 2004/0067000 A1 | 4/2004 | Bates et al. |
| 2004/0068161 A1 | 4/2004 | Couvillon |
| 2004/0082844 A1 | 4/2004 | Vardi et al. |
| 2004/0092830 A1 | 5/2004 | Scott et al. |
| 2004/0106853 A1 | 6/2004 | Moriyama |
| 2004/0111552 A1 | 6/2004 | Arimilli et al. |
| 2004/0126048 A1 | 7/2004 | Dave et al. |
| 2004/0143160 A1 | 7/2004 | Couvillon |
| 2004/0146546 A1 | 7/2004 | Gravett et al. |
| 2004/0186369 A1 | 9/2004 | Lam |
| 2004/0186558 A1 | 9/2004 | Pavcnik et al. |
| 2004/0195512 A1 | 10/2004 | Crosetto |
| 2004/0220606 A1 | 11/2004 | Goshgarian |
| 2004/0225220 A1 | 11/2004 | Rich |
| 2004/0239938 A1 | 12/2004 | Izatt |
| 2004/0242990 A1 | 12/2004 | Brister et al. |
| 2004/0248439 A1 | 12/2004 | Gernhardt et al. |
| 2004/0260236 A1 | 12/2004 | Manning et al. |
| 2005/0013778 A1 | 1/2005 | Green et al. |
| 2005/0031176 A1 | 2/2005 | Hertel et al. |
| 2005/0036150 A1 | 2/2005 | Izatt et al. |
| 2005/0078317 A1 | 4/2005 | Law et al. |
| 2005/0101859 A1 | 5/2005 | Maschke |
| 2005/0123180 A1 | 6/2005 | Luo |
| 2005/0140582 A1 | 6/2005 | Lee et al. |
| 2005/0140682 A1 | 6/2005 | Sumanaweera et al. |
| 2005/0140981 A1 | 6/2005 | Waelti |
| 2005/0140984 A1 | 6/2005 | Hitzenberger |
| 2005/0147303 A1 | 7/2005 | Zhou et al. |
| 2005/0165439 A1 | 7/2005 | Weber et al. |
| 2005/0171433 A1 | 8/2005 | Boppart et al. |
| 2005/0171438 A1 | 8/2005 | Chen et al. |
| 2005/0182297 A1 | 8/2005 | Gravenstein et al. |
| 2005/0196028 A1 | 9/2005 | Kleen et al. |
| 2005/0197585 A1 | 9/2005 | Brockway et al. |
| 2005/0213103 A1 | 9/2005 | Everett et al. |
| 2005/0215942 A1 | 9/2005 | Abrahamson et al. |
| 2005/0234445 A1 | 10/2005 | Conquergood et al. |
| 2005/0243322 A1 | 11/2005 | Lasker et al. |
| 2005/0249391 A1 | 11/2005 | Kimmel et al. |
| 2005/0251567 A1 | 11/2005 | Bellew et al. |
| 2005/0254059 A1 | 11/2005 | Alphonse |
| 2005/0264823 A1 | 12/2005 | Zhu et al. |
| 2006/0013523 A1 | 1/2006 | Childlers et al. |
| 2006/0015126 A1 | 1/2006 | Sher |
| 2006/0029634 A1 | 2/2006 | Berg et al. |
| 2006/0036167 A1 | 2/2006 | Shina |
| 2006/0038115 A1 | 2/2006 | Maas |
| 2006/0039004 A1 | 2/2006 | de Boer et al. |
| 2006/0041180 A1 | 2/2006 | Viswanathan et al. |
| 2006/0045536 A1 | 3/2006 | Arahira |
| 2006/0055936 A1 | 3/2006 | Yun et al. |
| 2006/0058622 A1 | 3/2006 | Tearney et al. |
| 2006/0064009 A1 | 3/2006 | Webler et al. |
| 2006/0067620 A1 | 3/2006 | Shishkov et al. |
| 2006/0072808 A1 | 4/2006 | Grimm et al. |
| 2006/0074442 A1 | 4/2006 | Noriega et al. |
| 2006/0098927 A1 | 5/2006 | Schmidt et al. |
| 2006/0100694 A1 | 5/2006 | Globerman |
| 2006/0106375 A1 | 5/2006 | Werneth et al. |
| 2006/0132790 A1 | 6/2006 | Gutin |
| 2006/0135870 A1 | 6/2006 | Webler |
| 2006/0142703 A1 | 6/2006 | Carter et al. |
| 2006/0142733 A1 | 6/2006 | Forsberg |
| 2006/0173299 A1 | 8/2006 | Romley et al. |
| 2006/0179255 A1 | 8/2006 | Yamazaki |
| 2006/0184048 A1 | 8/2006 | Saadat |
| 2006/0187537 A1 | 8/2006 | Huber et al. |
| 2006/0195269 A1 | 8/2006 | Yeatman et al. |
| 2006/0204119 A1 | 9/2006 | Feng et al. |
| 2006/0229591 A1 | 10/2006 | Lee |
| 2006/0239312 A1 | 10/2006 | Kewitsch et al. |
| 2006/0241342 A1 | 10/2006 | Macaulay et al. |
| 2006/0241465 A1 | 10/2006 | Huennekens et al. |
| 2006/0241503 A1 | 10/2006 | Schmitt et al. |
| 2006/0244973 A1 | 11/2006 | Yun et al. |
| 2006/0258895 A1 | 11/2006 | Maschke |
| 2006/0264743 A1 | 11/2006 | Kleen et al. |
| 2006/0267756 A1 | 11/2006 | Kates |
| 2006/0270976 A1 | 11/2006 | Savage et al. |
| 2006/0276709 A1 | 12/2006 | Khamene et al. |
| 2006/0279742 A1 | 12/2006 | Tearney et al. |
| 2006/0279743 A1 | 12/2006 | Boesser et al. |
| 2006/0285638 A1 | 12/2006 | Boese et al. |
| 2006/0287595 A1 | 12/2006 | Maschke |
| 2006/0293597 A1 | 12/2006 | Johnson et al. |
| 2007/0015969 A1 | 1/2007 | Feldman et al. |
| 2007/0016029 A1 | 1/2007 | Donaldson et al. |
| 2007/0016034 A1 | 1/2007 | Donaldson |
| 2007/0016062 A1 | 1/2007 | Park et al. |
| 2007/0027390 A1 | 2/2007 | Maschke et al. |
| 2007/0036417 A1 | 2/2007 | Argiro et al. |
| 2007/0038061 A1 | 2/2007 | Huennekens et al. |
| 2007/0038121 A1 | 2/2007 | Feldman et al. |
| 2007/0038125 A1 | 2/2007 | Kleen et al. |
| 2007/0043292 A1 | 2/2007 | Camus et al. |
| 2007/0043597 A1 | 2/2007 | Donaldson |
| 2007/0049847 A1 | 3/2007 | Osborne |
| 2007/0060973 A1 | 3/2007 | Ludvig et al. |
| 2007/0065077 A1 | 3/2007 | Childers et al. |
| 2007/0066888 A1 | 3/2007 | Maschke |
| 2007/0066890 A1 | 3/2007 | Maschke |
| 2007/0066983 A1 | 3/2007 | Maschke |
| 2007/0084995 A1 | 4/2007 | Newton et al. |
| 2007/0100226 A1 | 5/2007 | Yankelevitz et al. |
| 2007/0135887 A1 | 6/2007 | Maschke |
| 2007/0142707 A1 | 6/2007 | Wiklof et al. |
| 2007/0156019 A1 | 7/2007 | Larkin et al. |
| 2007/0161893 A1 | 7/2007 | Milner et al. |
| 2007/0161896 A1 | 7/2007 | Adachi et al. |
| 2007/0161963 A1 | 7/2007 | Smalling |
| 2007/0162860 A1 | 7/2007 | Muralidharan et al. |
| 2007/0165141 A1 | 7/2007 | Srinivas et al. |
| 2007/0167710 A1 | 7/2007 | Unal et al. |
| 2007/0167804 A1 | 7/2007 | Park et al. |
| 2007/0191682 A1 | 8/2007 | Rolland et al. |
| 2007/0201736 A1 | 8/2007 | Klingensmith et al. |
| 2007/0206193 A1 | 9/2007 | Pesach |
| 2007/0208276 A1 | 9/2007 | Kornkven Volk et al. |
| 2007/0225220 A1 | 9/2007 | Ming et al. |
| 2007/0225590 A1 | 9/2007 | Ramos |
| 2007/0229801 A1 | 10/2007 | Tearney et al. |
| 2007/0232872 A1 | 10/2007 | Prough et al. |
| 2007/0232874 A1 | 10/2007 | Ince |
| 2007/0232890 A1 | 10/2007 | Hirota |
| 2007/0232891 A1 | 10/2007 | Hirota |
| 2007/0232892 A1 | 10/2007 | Hirota |
| 2007/0232893 A1 | 10/2007 | Tanioka |
| 2007/0232933 A1 | 10/2007 | Gille et al. |
| 2007/0238957 A1 | 10/2007 | Yared |
| 2007/0239395 A1* | 10/2007 | Jenkins .................. A61B 5/107 702/158 |
| 2007/0247033 A1 | 10/2007 | Eidenschink et al. |
| 2007/0249967 A1* | 10/2007 | Buly et al. .................. 600/595 |
| 2007/0250000 A1 | 10/2007 | Magnin et al. |
| 2007/0250036 A1 | 10/2007 | Volk et al. |
| 2007/0258094 A1 | 11/2007 | Izatt et al. |
| 2007/0260138 A1 | 11/2007 | Feldman et al. |
| 2007/0278389 A1 | 12/2007 | Ajgaonkar et al. |

(56) References Cited

U.S. PATENT DOCUMENTS

| | | |
|---|---|---|
| 2007/0287914 A1 | 12/2007 | Cohen |
| 2008/0002183 A1 | 1/2008 | Yatagai et al. |
| 2008/0013093 A1 | 1/2008 | Izatt et al. |
| 2008/0021275 A1 | 1/2008 | Tearney et al. |
| 2008/0027481 A1 | 1/2008 | Gilson et al. |
| 2008/0043024 A1 | 2/2008 | Schiwietz et al. |
| 2008/0045842 A1 | 2/2008 | Furnish |
| 2008/0051660 A1 | 2/2008 | Kakadaris et al. |
| 2008/0063304 A1* | 3/2008 | Russak et al. ............... 382/298 |
| 2008/0085041 A1 | 4/2008 | Breeuwer |
| 2008/0095465 A1 | 4/2008 | Mullick et al. |
| 2008/0095714 A1 | 4/2008 | Castella et al. |
| 2008/0097194 A1 | 4/2008 | Milner |
| 2008/0101667 A1 | 5/2008 | Begelman et al. |
| 2008/0108867 A1 | 5/2008 | Zhou |
| 2008/0114254 A1 | 5/2008 | Matcovitch et al. |
| 2008/0119739 A1 | 5/2008 | Vardi et al. |
| 2008/0124495 A1 | 5/2008 | Horn et al. |
| 2008/0125772 A1 | 5/2008 | Stone et al. |
| 2008/0139897 A1 | 6/2008 | Ainsworth et al. |
| 2008/0143707 A1 | 6/2008 | Mitchell |
| 2008/0146941 A1 | 6/2008 | Dala-Krishna |
| 2008/0147111 A1 | 6/2008 | Johnson et al. |
| 2008/0154128 A1 | 6/2008 | Milner |
| 2008/0161696 A1 | 7/2008 | Schmitt et al. |
| 2008/0171944 A1 | 7/2008 | Brenneman et al. |
| 2008/0175465 A1 | 7/2008 | Jiang et al. |
| 2008/0177183 A1* | 7/2008 | Courtney ............ A61B 5/0062 600/463 |
| 2008/0180683 A1 | 7/2008 | Kemp |
| 2008/0181477 A1 | 7/2008 | Izatt et al. |
| 2008/0183075 A1* | 7/2008 | Govari ................. A61B 8/12 600/437 |
| 2008/0187201 A1 | 8/2008 | Liang et al. |
| 2008/0228086 A1 | 9/2008 | Ilegbusi et al. |
| 2008/0247622 A1 | 10/2008 | Aylward et al. |
| 2008/0247716 A1 | 10/2008 | Thomas et al. |
| 2008/0262470 A1 | 10/2008 | Lee et al. |
| 2008/0262489 A1 | 10/2008 | Steinke |
| 2008/0269599 A1 | 10/2008 | Csavoy et al. |
| 2008/0281205 A1 | 11/2008 | Naghavi et al. |
| 2008/0281248 A1 | 11/2008 | Angheloiu et al. |
| 2008/0285043 A1 | 11/2008 | Fercher et al. |
| 2008/0287795 A1 | 11/2008 | Klingensmith et al. |
| 2008/0291463 A1 | 11/2008 | Milner et al. |
| 2008/0292173 A1 | 11/2008 | Hsieh et al. |
| 2008/0294034 A1 | 11/2008 | Krueger et al. |
| 2008/0298655 A1 | 12/2008 | Edwards |
| 2008/0306766 A1 | 12/2008 | Ozeki et al. |
| 2009/0009801 A1 | 1/2009 | Tabuki |
| 2009/0018393 A1 | 1/2009 | Dick et al. |
| 2009/0034813 A1 | 2/2009 | Dikmen et al. |
| 2009/0043191 A1 | 2/2009 | Castella et al. |
| 2009/0046295 A1 | 2/2009 | Kemp et al. |
| 2009/0052614 A1 | 2/2009 | Hempel et al. |
| 2009/0069843 A1 | 3/2009 | Agnew |
| 2009/0079993 A1 | 3/2009 | Yatagai et al. |
| 2009/0088650 A1 | 4/2009 | Corl |
| 2009/0093980 A1 | 4/2009 | Kemp et al. |
| 2009/0122320 A1* | 5/2009 | Petersen ............ A61B 5/0066 356/477 |
| 2009/0138544 A1 | 5/2009 | Wegenkittl et al. |
| 2009/0149739 A9 | 6/2009 | Maschke |
| 2009/0156941 A1 | 6/2009 | Moore |
| 2009/0174886 A1 | 7/2009 | Inoue |
| 2009/0174931 A1 | 7/2009 | Huber et al. |
| 2009/0177090 A1 | 7/2009 | Grunwald et al. |
| 2009/0177183 A1 | 7/2009 | Pinkernell et al. |
| 2009/0195514 A1 | 8/2009 | Glynn et al. |
| 2009/0196470 A1 | 8/2009 | Carl et al. |
| 2009/0198125 A1 | 8/2009 | Nakabayashi et al. |
| 2009/0203991 A1 | 8/2009 | Papaioannou et al. |
| 2009/0264768 A1 | 10/2009 | Courtney et al. |
| 2009/0269014 A1 | 10/2009 | Winberg et al. |
| 2009/0270695 A1 | 10/2009 | McEowen |
| 2009/0284322 A1 | 11/2009 | Harrison et al. |
| 2009/0284332 A1 | 11/2009 | Moore et al. |
| 2009/0284749 A1 | 11/2009 | Johnson et al. |
| 2009/0290167 A1 | 11/2009 | Flanders et al. |
| 2009/0292048 A1 | 11/2009 | Li et al. |
| 2009/0299195 A1 | 12/2009 | Muller et al. |
| 2009/0299284 A1 | 12/2009 | Holman et al. |
| 2009/0318951 A1 | 12/2009 | Kashkarov et al. |
| 2009/0326634 A1 | 12/2009 | Vardi |
| 2010/0007669 A1 | 1/2010 | Bethune et al. |
| 2010/0030042 A1 | 2/2010 | Denninghoff et al. |
| 2010/0061611 A1 | 3/2010 | Xu et al. |
| 2010/0063400 A1 | 3/2010 | Hall et al. |
| 2010/0087732 A1 | 4/2010 | Eberle et al. |
| 2010/0094125 A1 | 4/2010 | Younge et al. |
| 2010/0094127 A1* | 4/2010 | Xu ..................... A61B 5/0066 600/425 |
| 2010/0094135 A1 | 4/2010 | Fang-Yen et al. |
| 2010/0094143 A1 | 4/2010 | Mahapatra et al. |
| 2010/0113919 A1 | 5/2010 | Maschke |
| 2010/0125238 A1 | 5/2010 | Lye et al. |
| 2010/0125268 A1 | 5/2010 | Gustus et al. |
| 2010/0125648 A1 | 5/2010 | Zaharia et al. |
| 2010/0128348 A1 | 5/2010 | Taverner |
| 2010/0152717 A1 | 6/2010 | Keeler |
| 2010/0160788 A1 | 6/2010 | Davies et al. |
| 2010/0161023 A1 | 6/2010 | Cohen et al. |
| 2010/0168714 A1 | 7/2010 | Burke et al. |
| 2010/0179421 A1 | 7/2010 | Tupin |
| 2010/0179426 A1 | 7/2010 | Davies et al. |
| 2010/0220334 A1 | 9/2010 | Condit et al. |
| 2010/0226607 A1 | 9/2010 | Zhang et al. |
| 2010/0234736 A1 | 9/2010 | Corl |
| 2010/0249601 A1 | 9/2010 | Courtney |
| 2010/0253949 A1* | 10/2010 | Adler .................. A61B 5/0066 356/479 |
| 2010/0256616 A1 | 10/2010 | Katoh et al. |
| 2010/0272432 A1 | 10/2010 | Johnson |
| 2010/0284590 A1 | 11/2010 | Peng et al. |
| 2010/0290693 A1 | 11/2010 | Cohen et al. |
| 2010/0331950 A1 | 12/2010 | Strommer |
| 2011/0010925 A1 | 1/2011 | Nix et al. |
| 2011/0021926 A1 | 1/2011 | Spencer et al. |
| 2011/0025853 A1 | 2/2011 | Richardson |
| 2011/0026797 A1 | 2/2011 | Declerck et al. |
| 2011/0032533 A1 | 2/2011 | Izatt et al. |
| 2011/0034801 A1 | 2/2011 | Baumgart |
| 2011/0044546 A1 | 2/2011 | Pan et al. |
| 2011/0066073 A1 | 3/2011 | Kuiper et al. |
| 2011/0071401 A1 | 3/2011 | Hastings et al. |
| 2011/0072405 A1 | 3/2011 | Chen et al. |
| 2011/0077528 A1 | 3/2011 | Kemp et al. |
| 2011/0080591 A1 | 4/2011 | Johnson et al. |
| 2011/0087104 A1 | 4/2011 | Moore et al. |
| 2011/0137140 A1 | 6/2011 | Tearney et al. |
| 2011/0144502 A1 | 6/2011 | Zhou et al. |
| 2011/0152771 A1 | 6/2011 | Milner et al. |
| 2011/0157597 A1 | 6/2011 | Lu et al. |
| 2011/0160586 A1 | 6/2011 | Li et al. |
| 2011/0178413 A1 | 7/2011 | Schmitt et al. |
| 2011/0190586 A1 | 8/2011 | Kemp |
| 2011/0191084 A1* | 8/2011 | Cooke ............................. 703/11 |
| 2011/0216378 A1 | 9/2011 | Poon et al. |
| 2011/0220985 A1 | 9/2011 | Son et al. |
| 2011/0238061 A1 | 9/2011 | van der Weide et al. |
| 2011/0238083 A1 | 9/2011 | Moll et al. |
| 2011/0245669 A1 | 10/2011 | Zhang |
| 2011/0249094 A1 | 10/2011 | Wang et al. |
| 2011/0257545 A1 | 10/2011 | Suri |
| 2011/0264125 A1 | 10/2011 | Wilson et al. |
| 2011/0274329 A1 | 11/2011 | Mathew et al. |
| 2011/0282334 A1 | 11/2011 | Groenhoff |
| 2011/0301684 A1 | 12/2011 | Fischell et al. |
| 2011/0306995 A1 | 12/2011 | Moberg |
| 2011/0319752 A1 | 12/2011 | Steinberg et al. |
| 2012/0004529 A1 | 1/2012 | Tolkowsky et al. |
| 2012/0004668 A1 | 1/2012 | Wallace et al. |
| 2012/0013914 A1 | 1/2012 | Kemp et al. |
| 2012/0016344 A1 | 1/2012 | Kusakabe |

(56) References Cited

U.S. PATENT DOCUMENTS

| | | |
|---|---|---|
| 2012/0016395 A1 | 1/2012 | Olson |
| 2012/0022360 A1 | 1/2012 | Kemp |
| 2012/0026503 A1 | 2/2012 | Lewandowski et al. |
| 2012/0029007 A1 | 2/2012 | Graham et al. |
| 2012/0059253 A1 | 3/2012 | Wang et al. |
| 2012/0059368 A1 | 3/2012 | Takaoka et al. |
| 2012/0062843 A1 | 3/2012 | Ferguson et al. |
| 2012/0065481 A1 | 3/2012 | Hunter et al. |
| 2012/0071823 A1 | 3/2012 | Chen |
| 2012/0071838 A1 | 3/2012 | Fojtik |
| 2012/0075638 A1* | 3/2012 | Rollins .............. A61B 1/00009 356/479 |
| 2012/0083696 A1 | 4/2012 | Kitamura |
| 2012/0095340 A1 | 4/2012 | Smith |
| 2012/0095372 A1 | 4/2012 | Sverdlik et al. |
| 2012/0108943 A1 | 5/2012 | Bates et al. |
| 2012/0113108 A1 | 5/2012 | Dala-Krishna |
| 2012/0116353 A1 | 5/2012 | Arnold et al. |
| 2012/0130243 A1 | 5/2012 | Balocco et al. |
| 2012/0130247 A1 | 5/2012 | Waters et al. |
| 2012/0136259 A1 | 5/2012 | Milner et al. |
| 2012/0136427 A1 | 5/2012 | Palmaz et al. |
| 2012/0137075 A1 | 5/2012 | Vorbach |
| 2012/0155734 A1 | 6/2012 | Barratt et al. |
| 2012/0158101 A1 | 6/2012 | Stone et al. |
| 2012/0162660 A1* | 6/2012 | Kemp ........................ 356/479 |
| 2012/0165661 A1 | 6/2012 | Kemp et al. |
| 2012/0170848 A1 | 7/2012 | Kemp et al. |
| 2012/0172698 A1 | 7/2012 | Teo et al. |
| 2012/0176607 A1 | 7/2012 | Ott |
| 2012/0184853 A1 | 7/2012 | Waters |
| 2012/0184859 A1 | 7/2012 | Shah et al. |
| 2012/0184977 A1 | 7/2012 | Wolf |
| 2012/0215094 A1 | 8/2012 | Rahimian et al. |
| 2012/0220836 A1 | 8/2012 | Alpert et al. |
| 2012/0220851 A1 | 8/2012 | Razansky et al. |
| 2012/0220865 A1 | 8/2012 | Brown et al. |
| 2012/0220874 A1 | 8/2012 | Hancock et al. |
| 2012/0220883 A1 | 8/2012 | Manstrom et al. |
| 2012/0224751 A1 | 9/2012 | Kemp et al. |
| 2012/0226153 A1 | 9/2012 | Brown et al. |
| 2012/0230565 A1 | 9/2012 | Steinberg et al. |
| 2012/0232400 A1 | 9/2012 | Dickinson et al. |
| 2012/0238869 A1 | 9/2012 | Schmitt et al. |
| 2012/0238956 A1 | 9/2012 | Yamada et al. |
| 2012/0244043 A1 | 9/2012 | Leblanc et al. |
| 2012/0250028 A1 | 10/2012 | Schmitt et al. |
| 2012/0253186 A1 | 10/2012 | Simpson et al. |
| 2012/0253192 A1 | 10/2012 | Cressman |
| 2012/0253276 A1 | 10/2012 | Govari et al. |
| 2012/0257210 A1 | 10/2012 | Whitney et al. |
| 2012/0262720 A1 | 10/2012 | Brown et al. |
| 2012/0265077 A1 | 10/2012 | Gille et al. |
| 2012/0265268 A1 | 10/2012 | Blum et al. |
| 2012/0265296 A1 | 10/2012 | McNamara et al. |
| 2012/0271170 A1 | 10/2012 | Emelianov et al. |
| 2012/0271175 A1 | 10/2012 | Moore et al. |
| 2012/0271339 A1 | 10/2012 | O'Beirne et al. |
| 2012/0274338 A1 | 11/2012 | Baks et al. |
| 2012/0276390 A1 | 11/2012 | Ji et al. |
| 2012/0277722 A1 | 11/2012 | Gerber et al. |
| 2012/0279764 A1 | 11/2012 | Jiang et al. |
| 2012/0283758 A1 | 11/2012 | Miller et al. |
| 2012/0289987 A1 | 11/2012 | Wilson et al. |
| 2012/0299439 A1 | 11/2012 | Huang |
| 2012/0310081 A1 | 12/2012 | Adler et al. |
| 2012/0310332 A1 | 12/2012 | Murray et al. |
| 2012/0319535 A1 | 12/2012 | Dausch |
| 2012/0323075 A1 | 12/2012 | Younge et al. |
| 2012/0323127 A1 | 12/2012 | Boyden et al. |
| 2012/0330141 A1 | 12/2012 | Brown et al. |
| 2013/0006105 A1* | 1/2013 | Furuichi .............. A61B 5/0066 600/427 |
| 2013/0015975 A1 | 1/2013 | Huennekens et al. |
| 2013/0023762 A1 | 1/2013 | Huennekens et al. |
| 2013/0023763 A1 | 1/2013 | Huennekens et al. |
| 2013/0026655 A1 | 1/2013 | Lee et al. |
| 2013/0030295 A1 | 1/2013 | Huennekens et al. |
| 2013/0030303 A1 | 1/2013 | Ahmed et al. |
| 2013/0030410 A1 | 1/2013 | Drasler et al. |
| 2013/0053949 A1 | 2/2013 | Pintor et al. |
| 2013/0109958 A1 | 5/2013 | Baumgart et al. |
| 2013/0109959 A1 | 5/2013 | Baumgart et al. |
| 2013/0137980 A1 | 5/2013 | Waters et al. |
| 2013/0150716 A1 | 6/2013 | Stigall et al. |
| 2013/0158594 A1 | 6/2013 | Carrison et al. |
| 2013/0218201 A1 | 8/2013 | Obermiller et al. |
| 2013/0218267 A1 | 8/2013 | Braido et al. |
| 2013/0223789 A1 | 8/2013 | Lee et al. |
| 2013/0223798 A1 | 8/2013 | Jenner et al. |
| 2013/0296704 A1 | 11/2013 | Magnin et al. |
| 2013/0303907 A1 | 11/2013 | Corl |
| 2013/0303920 A1 | 11/2013 | Corl |
| 2013/0310698 A1 | 11/2013 | Judell et al. |
| 2013/0331820 A1 | 12/2013 | Itou et al. |
| 2013/0338766 A1 | 12/2013 | Hastings et al. |
| 2013/0339958 A1 | 12/2013 | Droste et al. |
| 2014/0039294 A1 | 2/2014 | Jiang |
| 2014/0180067 A1 | 6/2014 | Stigall et al. |
| 2014/0180128 A1 | 6/2014 | Corl |
| 2014/0200438 A1 | 7/2014 | Millett et al. |

FOREIGN PATENT DOCUMENTS

| | | |
|---|---|---|
| EP | 2438877 A2 | 4/2012 |
| GB | 2280261 A | 1/1995 |
| JP | 2000-262461 A | 9/2000 |
| JP | 2000-292260 A | 10/2000 |
| JP | 2001-125009 A | 5/2001 |
| JP | 2001-272331 A | 10/2001 |
| JP | 2002-374034 A | 12/2002 |
| JP | 2003-143783 A | 5/2003 |
| JP | 2003-172690 A | 6/2003 |
| JP | 2003-256876 A | 9/2003 |
| JP | 2003-287534 A | 10/2003 |
| JP | 2005-274380 A | 10/2005 |
| JP | 2006-184284 A | 7/2006 |
| JP | 2006-266797 A | 10/2006 |
| JP | 2006-313158 A | 11/2006 |
| JP | 2007-024677 A | 2/2007 |
| JP | 2009-233001 A | 10/2009 |
| JP | 2011-56786 A | 3/2011 |
| WO | 91/01156 A1 | 2/1991 |
| WO | 92/16865 A1 | 10/1992 |
| WO | 93/06213 A1 | 4/1993 |
| WO | 93/08829 A1 | 5/1993 |
| WO | 98/38907 A1 | 9/1998 |
| WO | 98/57583 A1 | 12/1998 |
| WO | 00/11511 A1 | 3/2000 |
| WO | 00/044296 A1 | 8/2000 |
| WO | 01/11409 A2 | 2/2001 |
| WO | 03/062802 A2 | 7/2003 |
| WO | 03/073950 A1 | 9/2003 |
| WO | 2004/010856 A1 | 2/2004 |
| WO | 2004/023992 A1 | 3/2004 |
| WO | 2004/096049 A2 | 11/2004 |
| WO | 2005/047813 A1 | 5/2005 |
| WO | 2005/106695 A2 | 11/2005 |
| WO | 2006/029634 A2 | 3/2006 |
| WO | 2006/037132 A1 | 4/2006 |
| WO | 2006/039091 A2 | 4/2006 |
| WO | 2006/061829 A1 | 6/2006 |
| WO | 2006/068875 A2 | 6/2006 |
| WO | 2006/111704 A1 | 10/2006 |
| WO | 2006/119416 A2 | 11/2006 |
| WO | 2006/121851 A2 | 11/2006 |
| WO | 2006/130802 A2 | 12/2006 |
| WO | 2007/002685 A2 | 1/2007 |
| WO | 2007/025230 A2 | 3/2007 |
| WO | 2007/045690 A1 | 4/2007 |
| WO | 2007/058895 A2 | 5/2007 |
| WO | 2007/067323 A2 | 6/2007 |
| WO | 2007/084995 A2 | 7/2007 |
| WO | 2008/058084 A2 | 5/2008 |

(56) References Cited

FOREIGN PATENT DOCUMENTS

| | | |
|---|---|---|
| WO | 2008/069991 A1 | 6/2008 |
| WO | 2008/107905 A2 | 9/2008 |
| WO | 2009/009799 A1 | 1/2009 |
| WO | 2009/009801 A1 | 1/2009 |
| WO | 2009/046431 A1 | 4/2009 |
| WO | 2009/121067 A1 | 10/2009 |
| WO | 2009/137704 A1 | 11/2009 |
| WO | 2011/06886 A2 | 1/2011 |
| WO | 2011/038048 A1 | 3/2011 |
| WO | 2011/081688 A1 | 7/2011 |
| WO | 2012/003369 A2 | 1/2012 |
| WO | 2012/061935 A1 | 5/2012 |
| WO | 2012/071388 A2 | 5/2012 |
| WO | 2012/087818 A1 | 6/2012 |
| WO | 2012/098194 A1 | 7/2012 |
| WO | 2012/109676 A1 | 8/2012 |
| WO | 2012/130289 A1 | 10/2012 |
| WO | 2012/154767 A2 | 11/2012 |
| WO | 2012/155040 A1 | 11/2012 |
| WO | 2013/033414 A1 | 3/2013 |
| WO | 2013/033415 A2 | 3/2013 |
| WO | 2013/033418 A1 | 3/2013 |
| WO | 2013/033489 A1 | 3/2013 |
| WO | 2013/033490 A1 | 3/2013 |
| WO | 2013/033592 A1 | 3/2013 |
| WO | 2013/126390 A1 | 8/2013 |
| WO | 2014/109879 A1 | 7/2014 |

OTHER PUBLICATIONS

Tommasini, Giorgio, Paolo Rubartelli, and Maurizio Piaggio. "A deterministic approach to automated stenosis quantification." Catheterization and Cardiovascular Interventions 48.4 (1999): 435-445.*

Sihan et al., 2008, A novel approach to quantitative analysis of intraluminal optical coherence tomography imaging, Comput. Cardiol:1089-1092.

Siwy et al., 2003, Electro-responsive asymmetric nanopores in polyimide with stable ion-current signal, Applied Physics A: Materials Science & Processing 76:781-785.

Smith et al., 1989, Absolute displacement measurements using modulation of the spectrum of white light in a Michelsor interferometer, Applied Optics, 28(16):3339-3342.

Smith, 1997, The Scientist and Engineer's Guide to Digital Signal Processing, California Technical Publishing, San Diego, CA:432-436.

Soller, 2003, Polarization diverse optical frequency domain interferometry:All coupler implementation, Bragg Grating, Photosensitivity, and Poling in Glass Waveguides Conference MB4:30-32.

Song et al., 2012, Active tremor cancellation by a "Smart" handheld vitreoretinal microsurgical tool using swept source optical coherence tomography, Optics Express, 20(21):23414-23421.

Stenqvist et al., 1983, Stiffness of central venous catheters, Acta Anaesthesiol Scand., 2:153-157.

Strickland, 1970, Time-Domain Reflectometer Measurements, Tektronix, Beaverton, OR, (107 pages).

Strobl et al., 2009, An Introduction to Recursive Partitioning:Rationale, Application and Characteristics of Classification and Regression Trees, Bagging and Random Forests, Psychol Methods., 14(4):323-348.

Sutcliffe et al., 1986, Dynamics of UV laser ablation of organic polymer surfaces, Journal of Applied Physics, 60(9):3315-3322.

Suzuki, 2013, A novel guidewire approach for handling acute-angle bifurcations, J Inv Cardiol 25(1):48-54.

Tanimoto et al., 2008, A novel approach for quantitative analysis of intracoronary optical coherence tomography: high inter-observer agreement with computer-assisted contour detection, Cathet Cardiovascular Intervent., 72(2):228-235.

Tearney et al., 1997, In vivo Endoscopic Optical Biopsy with Optical Coherence Tomography, Science, 276:2037-2039.

Tonino et al., 2009, Fractional flow reserve versus angiography for guiding percutaneous coronary intervention, The New England Journal of Medicine, 360:213-224.

Toregeani et al., 2008, Evaluation of hemodialysis arteriovenous fistula maturation by color-flow Doppler ultrasound, J Vasc. Bras. 7(3):203-213.

Translation of Notice of Reason(s) for Refusal dated Apr. 30, 2014, for Japanese Patent Application No. 2011-508677, (5 pages).

Translation of Notice of Reason(s) for Refusal dated May 25, 2012, for Japanese Patent Application No. 2009-536425, (3 pages).

Translation of Notice of Reason(s) for Refusal dated Nov. 22, 2012, for Japanese Patent Application No. 2010-516304, (6 pages).

Traunecker et al., 1991, Bispecific single chain molecules (Janusins) target cytotoxic lymphocytes on HIV infected cells EMBO J., 10:3655-3659.

Trolier-McKinstry et. al., 2004, Thin Film Piezoelectric for MEMS, Journal of Electroceramics 12:7-17.

Tuniz et al., 2010, Weaving the invisible thread: design of an optically invisible metamaterial fibre, Optics Express 18(17):18095-18105.

Turk et al., 1991, Eigenfaces for Recognition, Journal of Cognitive Neuroscience 3(1):71-86.

Tuzel et al., 2006, Region Covariance: A Fast Descriptor for Detection and Classification, European Conference on Computer Vision (ECCV).

Urban et al., 2010, Design of a Pressure Sensor Based on Optical Bragg Grating Lateral Deformation, Sensors (Basel), 10(12):11212-11225.

Vakhtin et al., 2003, Common-path interferometer for frequency-domain optical coherence tomography, Applied Optics, 42(34):6953-6958.

Vakoc et al., 2005, Phase-Resolved Optical Frequency Domain Imaging, Optics Express 13(14):5483-5493.

Verhoeyen et al., 1988, Reshaping human antibodies: grafting an antilysozyme activity, Science, 239:1534-1536.

Villard et al., 2002, Use of a blood substitute to determine instantaneous murine right ventricular thickening with optical coherence tomography, Circulation, 105:1843-1849.

Wang et al., 2002, Optimizing the Beam Patten of a Forward-Viewing Ring-Annular Ultrasound Array for Intravascular Imaging, Transactions on Ultrasonics, Ferroelectrics, and Frequency Control, 49(12).

Wang et al., 2006, Multiple biomarkers for the prediction of first major cardiovascular events and death, The New England Journal of Medicine, 355(25):2631-2639.

Wang et al., 2009, Robust Guidewire Tracking in Fluoroscopy, IEEE Conference on Computer Vision and Pattern Recognition—CVPR 2009:691-698.

Wang et al., 2011, In vivo intracardiac optical coherence tomography imaging through percutaneous access: toward image-guided radio-frequency ablation, J. Biomed. Opt. 0001 16(11):110505-1 (3 pages).

Waterhouse et. al., 1993, Combinatorial infection and in vivo recombination: a strategy for making large phage antibody repertoires, Nucleic Acids Res., 21:2265-2266.

Wegener, 2011, 3D Photonic Metamaterials and Invisibility Cloaks: The Method of Making, MEMS 2011, Cancun, Mexico, Jan. 23-27, 2011.

West et al., 1991, Arterial insufficiency in hemodialysis access procedures: correction by banding technique, Transpl Proc 23(2):1838-40.

Wyawahare et al., 2009, Image registration techniques: an overview, International Journal of Signal Processing, Image Processing and Pattern Recognition, 2(3):11-28.

Yaqoob et al., 2006, Methods and application areas of endoscopic optical coherence tomography, J. Biomed. Opt., 11, 063001-1-063001-19.

Yasuno et al., 2004, Polarization-sensitive complex Fourier domain optical coherence tomography for Jones matrix imaging of biological samples, Applied Physics Letters 85(15):3023-3025.

Zhang et al., 2004, Full range polarization-sensitive Fourier domain optical coherence tomography, Optics Express, 12(24):6033-6039.

(56) References Cited

OTHER PUBLICATIONS

Zitova et al., 2003, Image registration methods: A survey. Image and Vision Computing, 21(11):977-1000.

Abdi et al., 2010, Principal component analysis, Wiley Interdisciplinary Reviews: Computational Statistics 2:433-459.

Adler et al., 2007, Phase-Sensitive Optical Coherence Tomography at up to 370,000 Lines Per Second Using Buffered Fourier Domain Mode-Locked Lasers, Optics Letters, 32(6):626-628.

Agresti, 1996, Models for Matched Pairs, Chapter 8, An Introduction to Categorical Data Analysis, Wiley-Interscience A John Wiley & Sons, Inc., Publication, Hoboken, New Jersey.

Akasheh et al., 2004, Development of piezoelectric micromachined ultrasonic transducers, Sensors and Actuators A Physical, 111:275-287.

Amini et al., 1990, Using dynamic programming for solving variational problems in vision, IEEE Transactions on Pattern Analysis and Machine Intelligence, 12(9):855-867.

Bail et al., 1996, Optical coherence tomography with the "Spectral Radar"—Fast optical analysis in volume scatterers by short coherence interferometry, Optics Letters 21(14):1087-1089.

Bain, 2011, Privacy protection and face recognition, Chapter 3, Handbook of Face Recognition, Stan et al., Springer-Verlag.

Barnea et al., 1972, A class of algorithms for fast digital image registration, IEEE Trans. Computers, 21(2):179-186.

Blanchet et al., 1993, Laser Ablation and the Production of Polymer Films, Science, 262(5134):719-721.

Bonnema, 2008, Imaging Tissue Engineered Blood Vessel Mimics with Optical Tomography, College of Optical Sciences dissertation, University of Arizona (252 pages).

Bouma et al., 1999, Power-efficient nonreciprocal interferometer and linear-scanning fiber-optic catheter for optical coherence tomography, Optics Letters, 24(8):531-533.

Breiman, 2001, Random forests, Machine Learning 45:5-32.

Brown, 1992, A survey of image registration techniques, ACM Computing Surveys 24(4):325-376.

Bruining et al., 2009, Intravascular Ultrasound Registration/Integration with Coronary Angiography, Cardiology Clinics, 27(3):531-540.

Brummer, 1997, An euclidean distance measure between covariance matrices of speechcepstra for text-independent speaker recognition, in Proc. South African Symp. Communications and Signal Processing:167-172.

Burr et al., 2005, Searching for the Center of an Ellipse in Proceedings of the 17th Canadian Conference on Computational Geometry:260-263.

Canny, 1986, A computational approach to edge detection, IEEE Trans. Pattern Anal. Mach. Intell. 8:679-698.

Cavalli et al., 2010, Nanosponge formulations as oxygen delivery systems, International Journal of Pharmaceutics 402:254-257.

Choma et al., 2003, Sensitivity Advantage of Swept Source and Fourier Domain Optical Coherence Tomography, Optics Express 11(18):2183-2189.

Clarke et al., 1995, Hypoxia and myocardial ischaemia during peripheral angioplasty, Clinical Radiology, 50(5):301-303.

Collins, 1993, Coronary flow reserve, British Heart Journal 69:279-281.

Communication Mechanisms for Distributed Real-Time Applications, NI Developer Zone, http://zone.ni.eom/devzone/cda/tut/p/id/3105, accessed Jul. 23, 2007.

Cook, 2007, Use and misuse of receiver operating characteristic curve in risk prediction, Circulation 115(7):928-35.

D'Agostino et al., 2001, Validation of the Framingham coronary heart disease prediction score: results of a multiple ethnic group investigation, JAMA 286:180-187.

David et al., 1974, Protein iodination with solid-state lactoperoxidase, Biochemistry 13:1014-1021.

Davies et al., 1985, Plaque fissuring—the cause of acute myocardial infarction, sudden ischaemic death, and crescendo angina, British Heart Journal 53:363-373.

Davies et al., 1993, Risk of thrombosis in human atherosclerotic plaques: role of extracellular lipid, macrophage, and smooth muscle cell content, British Heart Journal 69:377-381.

Deterministic Data Streaming in Distributed Data Acquisition Systems, NI Developer Zone, "What is Developer Zone?", http://zone.ni.eom/devzone/cda/tut/p/id/3105, accessed Jul. 23, 2007.

Eigenwillig, 2008, K-Space Linear Fourier Domain Mode Locked Laser and Applications for Optical Coherence Tomography, Optics Express 16(12):8916-8937.

Elghanian et al., 1997, Selective colorimetric detection of polynucleotides based on the distance-dependent optical properties of gold nanoparticles, Science, 277(5329):1078-1080.

Ergun et al., 2003, Capacitive Micromachined Ultrasonic Transducers:Theory and Technology, Journal of Aerospace Engineering, 16(2):76-84.

Evans et al., 2006, Optical coherence tomography to identify intramucosa carcinoma and high-grade dysplasia in Barrett's esophagus, Clin Gast Hepat 4(1):38-43.

Fatemi et al., 1999, Vibro-acoustography: an imaging modality based on ultrasound-stimulated acoustic emission, PNAS U.S.A., 9(12):6603-6608.

Felzenszwalb et al., 2005, Pictorial Structures for Object Recognition, International Journal of Computer Vision, 61(1):55-79.

Ferring et al., 2008, Vasculature ultrasound for the pre-operative evaluation prior to arteriovenous fistula formation for haemodialysis: review of the evidence, Nephrol. Dial. Transplant. 23(6):1809-1815.

Fischler et al., 1973, The representation and matching of pictorial structures, IEEE Transactions on Computer 22:67-92.

Fleming et al., 2010, Real-time monitoring of cardiac radiofrequency ablation lesion formation using an optical coherence tomography forward-imaging catheter, Journal of Biomedical Optics 15 (3):030516-1 (3 pages).

Fookes et al., 2002, Rigid and non-rigid image registration and its association with mutual information:A review, Technical Report ISBN:1 86435 569 7, RCCVA, QUT.

Forstner & Moonen, 1999, A metric for covariance matrices, In Technical Report of the Dpt of Geodesy and Geoinformatics, Stuttgart University, 113-128.

Goel et al., 2006, Minimally Invasive Limited Ligation Endoluminal-assisted Revision (MILLER) for treatment of dialysis access-associated steal syndrome, Kidney Int 70(4):765-70.

Gotzinger et al., 2005, High speed spectral domain polarization sensitive optical coherence tomography of the human retina, Optics Express 13(25):10217-10229.

Gould et al., 1974, Physiologic basis for assessing critical coronary stenosis, American Journal of Cardiology, 33:87-94.

Griffiths et al., 1993, Human anti-self antibodies with high specificity from phage display libraries, The EMBO Journal, 12:725-734.

Griffiths et al., 1994, Isolation of high affinity human antibodies directly from large synthetic repertoires, The EMBO Journal, 13(14):3245-3260.

Grund et al., 2010, Analysis of biomarker data:logs, odds, ratios and ROC curves, Curr Opin HIV AIDS 5(6):473-479.

Harrison et al., 2011, Guidewire Stiffness: What's in a name?, J Endovasc Ther, 18(6):797-801.

Huber et al., 2005, Amplified, Frequency Swept Lasers for Frequency Domain Reflectometry and OCT Imaging: Design and Scaling Principles, Optics Express 13(9):3513-3528.

Huber et al., 2006, Fourier Domain Mode Locking (FDML): A New Laser Operating Regime and Applications for Optica Coherence Tomography, Optics Express 14(8):3225-3237.

International Search Report and Written Opinion dated Mar. 11, 2014, for International Patent Application No. PCT/US13/75675, filed Dec. 17, 2013 (7 pages).

International Search Report and Written Opinion dated Mar. 19, 2014, for International Patent Application No. PCT/US13/075353, filed Dec. 16, 2013 (8 pages).

International Search Report and Written Opinion dated Nov. 2, 2012, for International Patent Application No. PCT/US12/53168, filed Aug. 30, 2013 (8 pages).

International Search Report and Written Opinion dated Apr. 14, 2014, for International Patent Application No. PCT/US2013/076148, filed Dec. 18, 2013 (8 pages).

(56) References Cited

OTHER PUBLICATIONS

International Search Report and Written Opinion dated Apr. 21, 2014, for International Patent Application No. PCT/US2013/076015, filed Dec. 18, 2013 (7 pages).
International Search Report and Written Opinion dated Apr. 23, 2014, for International Patent Application No. PCT/US2013/075328, filed Dec. 16, 2013 (8 pages).
International Search Report and Written Opinion dated Apr. 29, 2014, for International Patent Application No. PCT/US13/76093, filed Dec. 18, 2013 (6 pages).
International Search Report and Written Opinion dated Apr. 9, 2014, for International Patent Application No. PCT/US13/75089, filed Dec. 13, 2013 (7 pages).
International Search Report and Written Opinion dated Feb. 21, 2014, for International Patent Application No. PCT/US13/76053, filed Dec. 18, 2013 (9 pages).
International Search Report and Written Opinion dated Feb. 21, 2014, for International Patent Application No. PCT/US2013/076965, filed Dec. 20, 2013 (6 pages).
International Search Report and Written Opinion dated Feb. 27, 2014, for International Patent Application No. PCT/US13/75416, filed Dec. 16, 2013 (7 pages).
International Search Report and Written Opinion dated Feb. 28, 2014, for International Patent Application No. PCT/US13/75653, filed Dec. 17, 2013 (7 pages).
International Search Report and Written Opinion dated Feb. 28, 2014, for International Patent Application No. PCT/US13/75990, filed Dec. 18, 2013 (7 pages).
International Search Report and Written Opinion dated Jan. 16, 2009, for International Patent Application No. PCT/US08/78963 filed on Oct. 6, 2008 (7 pages).
International Search Report and Written Opinion dated Jul. 30, 2014, for International Patent Application No. PCT/US14/21659, filed Mar. 7, 2014 (15 pages).
International Search Report and Written Opinion dated Mar. 10, 2014, for International Patent Application No. PCT/US2013/076212, filed Dec. 18, 2013 (8 pages).
International Search Report and Written Opinion dated Mar. 11, 2014, for International Patent Application No. PCT/US13/76173, filed Dec. 16, 2013 (9 pages).
International Search Report and Written Opinion dated Mar. 11, 2014, for International Patent Application No. PCT/US13/76449, filed Dec. 19, 2013 (9 pages).
International Search Report and Written Opinion dated Mar. 18, 2014, for International Patent Application No. PCT/US2013/076502, filed Dec. 19, 2013 (7 pages).
International Search Report and Written Opinion dated Mar. 18, 2014, for International Patent Application No. PCT/US2013/076788, filed Dec. 20, 2013 (7 pages).
International Search Report and Written Opinion dated Mar. 19, 2014, for International Patent Application No. PCT/US13/75349, filed Dec. 16, 2013 (10 pages).
International Search Report and Written Opinion dated Mar. 19, 2014, for International Patent Application No. PCT/US2013/076587, filed Dec. 19, 2013 (10 pages).
International Search Report and Written Opinion dated Mar. 19, 2014, for International Patent Application No. PCT/US2013/076909, filed Dec. 20, 2013 (7 pages).
International Search Report and Written Opinion dated Mar. 7, 2014, for International Patent Application No. PCT/US2013/076304, filed Dec. 18, 2013 (9 pages).
International Search Report and Written Opinion dated Mar. 7, 2014, for International Patent Application No. PCT/US2013/076480, filed Dec. 19, 2013 (8 pages).
International Search Report and Written Opinion dated Mar. 7, 2014, for International Patent Application No. PCT/US2013/076512, filed Dec. 19, 2013 (8 pages).
International Search Report and Written Opinion dated Mar. 7, 2014, for International Patent Application No. PCT/US2013/076531, filed Dec. 19, 2013 (10 pages).
Jakobovits et al., 1993, Analysis of homozygous mutant chimeric mice:deletion of the immunoglobulin heavy-chain joining region blocks B-cell development and antibody production, PNAS USA 90:2551-255.
Jakobovits et al., 1993, Germ-line transmission and expression of a human-derived yeast artificial chromosome, Nature 362:255-258.
Jang et al., 2002, Visualization of Coronary Atherosclerotic Plaques in Patients Using Optical Coherence Tomography: Comparison With Intravascular Ultrasound, Journal of the American College of Cardiology 39:604-609.
Jiang et al., 1992, Image registration of multimodality 3-D medical images by chamfer matching, Proc. SPIE 1660, Biomedical Image Processing and Three-Dimensional Microscopy, 356-366.
Johnson et al., 1993, Human antibody engineering: Current Opinion in Structural Biology, 3:564-571.
Jones et al., 1986, Replacing the complementarity-determining regions in a human antibody with those from a mouse, Nature, 321:522-525.
Juviler et al., 2008, Anorectal sepsis and fistula-in-ano, Surgical Technology International, 17:139-149.
Karapatis et al., 1998, Direct rapid tooling:a review of current research, Rapid Prototyping Journal, 4(2):77-89.
Karp et al., 2009, The benefit of time-of-flight in PET imaging, J Nucl Med 49:462-470.
Kelly et al., 2005, Detection of Vascular Adhesion Molecule-1 Expression Using a Novel Multimodal Nanoparticle, Circulation Research 96:327-336.
Kemp et al., 2005, Depth Resolved Optic Axis Orientation in Multiple Layered Anisotropic Tissues Measured with Enhanced Polarization Sensitive Optical Coherence Tomography, Optics Express 13(12):4507-4518.
Kersey et al., 1991, Polarization insensitive fiber optic Michelson interferometer, Electron. Lett. 27:518-520.
Kheir et al., 2012, Oxygen Gas-Filled Microparticles Provide Intravenous Oxygen Delivery, Science Translational Medicine 4(140):140ra88 (10 pages).
Khuri-Yakub et al., 2011, Capacitive micromachined ultrasonic transducers for medical imaging and therapy, J Micromech Microeng. 21(5):054004-054014.
Kirkman, 1991, Technique for flow reduction in dialysis access fistulas, Surg Gyn Obstet, 172(3):231-3.
Kohler et al., 1975, Continuous cultures of fused cells secreting antibody of predefined specificity, Nature, 256:495-7.
Koo et al., 2011, Diagnosis of IschemiaCausing Coronary Stenoses by Noninvasive Fractional Flow Reserve Computed From Coronary Computed Tomographic Angiograms, J Am Coll Cardiol 58(19):1989-1997.
Kozbor et al., 1984, A human hybrid myeloma for production of human monoclonal antibodies, J. Immunol., 133:3001-3005.
Kruth et al., 2003, Lasers and materials in selective laser sintering, Assembly Automation, 23(4):357-371.
Kumagai et al., 1994, Ablation of polymer films by a femtosecond high-peak-power Ti:sapphire laser at 798 nm, Applied Physics Letters, 65(14):1850-1852.
Larin et al., 2002, Noninvasive Blood Glucose Monitoring with Optical Coherence Tomography: a pilot study in human subjects, Diabetes Care, 25(12):2263-7.
Larin et al., 2004, Measurement of Refractive Index Variation of Physiological Analytes using Differential Phase OCT, Proc of SPIE 5325:31-34.
Laufer, 1996, Introduction to Optics and Lasers in Engineering, Cambridge University Press, Cambridge UK:156-162.
Lefevre et al., 2001, Stenting of bifurcation lesions:a rational approach, J. Interv. Cardiol., 14(6):573-585.
Li et al., 2000, Optical Coherence Tomography: Advanced Technology for the Endoscopic Imaging of Barrett's Esophagus, Endoscopy, 32(12):921-930.
Little et al., 1991, The underlying coronary lesion in myocardial infarction:implications for coronary angiography, Clinical Cardiology, 14(11):868-874.
Loo, 2004, Nanoshell Enabled Photonics-Based Imaging and Therapy of Cancer, Technology in Cancer Research & Treatment 3(1):33-40.

(56) References Cited

OTHER PUBLICATIONS

Machine translation of JP 2000-097846, (original JP 2000-097846 published Apr. 7, 2000).
Machine translation of JP 2000-321034, (original JP 2000-321034 published Nov. 24, 2000).
Machine translation of JP 2000-329534, (original JP 2000-329534 published Nov. 30, 2000).
Machine translation of JP 2004-004080, (original JP 2004-004080 published Jan. 8, 2004).
Maintz et al., 1998, An Overview of Medical Image Registration Methods, Technical Report UU-CS, (22 pages).
Mamas et al., 2010, Resting Pd/Pa measured with intracoronary pressure wire strongly predicts fractional flow reserve, Journal of Invasive Cardiology 22(6):260-265.
Marks et al., 1991, By-passing Immunization Human Antibodies from V-gene Libraries Displayed on Phage, J. Mol. Biol. 222:581-597.
Marks et al., 1992, By-Passing Immunization:Building High Affinity Human Antibodies by Chain Shuffling, BioTechnol., 10:779-783.
Maruno et al., 1991, Fluorine containing optical adhesives for optical communications systems, J. Appl. Polymer. Sci. 42:2141-2148.
McCafferty et al., 1990, Phage antibodies: filamentous phage displaying antibody variable domains, Nature 348:552-554.
Mendieta et al., 1996, Complementary sequence correlations with applications to reflectometry studies, Instrumentation and Development 3(6):37-46.
Mickley, 2008, Steal Syndrome-strategies to preserve vascular access and extremity, Nephrol Dial Transplant 23:19-24.
Miller et al., 2010, The MILLER banding procedure is an effective method for treating dialysis-associated steal syndrome, Kidney International 77:359-366.
Milstein et al., 1983, Hybrid hybridomas and their use in immunohistochemistry, Nature 305:537-540.
Mindlin et al., 1936, A force at a point of a semi-infinite solid, Physics, 7:195-202.
Morrison et al., 1984, Chimeric human antibody molecules: mouse antigen-binding domains with human constant region domains, PNAS 81:6851-6855.
Munson et al., 1980, Ligand: a versatile computerized approach for characterization of ligand-binding systems, Analytical Biochemistry, 107:220-239.
Nezam, 2008, High Speed Polygon-Scanner-Based Wavelength-Swept Laser Source in the Telescope—Less Configurations with Application in Optical Coherence Tomography, Optics Letters 33(15):1741-1743.
Nissen, 2001, Coronary Angiography and Intravascular Ultrasound, American Journal of Cardiology, 87(suppl):15A-20A.
Nitenberg et al., 1995, Coronary vascular reserve in humans: a critical review of methods of evaluation and of interpretation of the results, Eur Heart J. 16(Suppl 1):7-21.
Notice of Reason(s) for Refusal dated Apr. 30, 2013, for Japanese Patent Application No. 2011-508677 for Optical Imaging Catheter for Aberation Balancing to Volcano Corporation, which application is a Japanese national stage entry of PCT/US2009/043181 with international filing date May 7, 2009, of the same title, published on Nov. 12, 2009, as WO 2009/137704, and accompanying English translation of the Notice of Reason(s) for Refusal and machine translations of JP11-56786 and JP2004-290548 (56 pages).
Nygren, 1982, Conjugation of horseradish peroxidase to Fab fragments with different homobifunctional and heterobifunctional cross-linking reagents. A comparative study, J. Histochem. and Cytochem. 30:407-412.
Oesterle et al., 1986, Angioplasty at coronary bifurcations: single-guide, two-wire technique, Cathet Cardiovasc Diagn., 12:57-63.
Okuno et al., 2003, Recent Advances in Optical Switches Using Silica-based PLC Technology, NTT Technical Review 1(7):20-30.
Oldenburg et al., 1998, Nanoengineering of Optical Resonances, Chemical Physics Letters 288:243-247.
Oldenburg et al., 2003, Fast-Fourier-Domain Delay Line for In Vivo Optical Coherence Tomography with a Polygonal Scanner, Applied Optics, 42(22):4606-4611.
Othonos, 1997, Fiber Bragg gratings, Review of Scientific Instruments 68(12):4309-4341.
Owens et al., 2007, A Survey of General-Purpose Computation on Graphics Hardware, Computer Graphics Forum 26(1):80-113.
Pain et al., 1981, Preparation of protein A-peroxidase mono conjugate using a heterobifunctional reagent, and its use it enzyme immunoassays, J Immunol Methods, 40:219-30.
Park et al., 2005, Real-time fiber-based multi-functional spectral-domain optical coherence tomography at 1.3 um., Optics Express 13(11):3931-3944.
Pasquesi et al., 2006, In vivo detection of exercise induced ultrastructural changes in genetically-altered murine skeletal muscle using polarization-sensitive optical coherence tomography, Optics Express 14(4):1547-1556.
Pepe et al., 2004, Limitations of the odds ratio in gauging the performance of a diagnostic, prognostic, or screening marker, American Journal of Epidemiology 159(9):882-890.
Persson et al., 1985, Acoustic impedance matching of medical ultrasound transducers, Ultrasonics, 23(2):83-89.
Placht et al., 2012, Fast time-of-flight camera based surface registration for radiotherapy patient positioning, Medical Physics 39(1):4-17.
Rabbani et al., 1999, Review: Strategies to achieve coronary arterial plaque stabilization, Cardiovascular Research 41:402-417.
Radvany et al., 2008, Plaque Excision in Management of Lower Extremity Peripheral Arterial Disease with the SilverHawk Atherectomy Catheter, Seminars in Interventional Radiology, 25(1):11-19.
Reddy et al., 1996, An FFT-Based Technique for Translation, Rotation, and Scale-Invariant Image Registration, IEEE Transaction on Image Processing 5(8):1266-1271.
Riechmann et al., 1988, Reshaping human antibodies for therapy, Nature, 332:323-327.
Rivers et al., 1992, Correction of steal syndrome secondary to hemodialysis access fistulas: a simplified quantitative technique, Surgery, 112(3):593-7.
Robbin et al., 2002, Hemodialysis Arteriovenous Fistula Maturity: US Evaluation, Radiology 225:59-64.
Rollins et al., 1998, In vivo video rate optical coherence tomography, Optics Express 3:219-229.
Sarunic et al., 2005, Instantaneous Complex Conjugate Resolved Spectral Domain and Swept-Source OCT Using 3×3 Fiber Couplers, Optics Express 13(3):957-967.
Satiani et al., 2009, Predicted Shortage of Vascular Surgeons in the United States, J. Vascular Surgery 50:946-952.
Schneider et al., 2006, T-banding: A technique for flow reduction of a hyper-functioning arteriovenous fistula, J Vasc Surg. 43(2):402-405.
Sen et al., 2012, Development and validation of a new adenosine-independent index of stenosis severity from coronary wave-intensity analysis, Journal of the American College of Cardiology 59(15):1392-1402.
Setta et al., 2005, Soft versus firm embryo transfer catheters for assisted reproduction: a systematic review and meta-analysis, Human Reproduction, 20(11):3114-3121.
Seward et al., 1996, Ultrasound Cardioscopy: Embarking on New Journey, Mayo Clinic Proceedings 71(7):629-635.
Shen et al., 2006, Eigengene-based linear discriminant model for tumor classification using gene expression microarray data, Bioinformatics 22(21):2635-2642.

\* cited by examiner

MANUAL CALIBRATION OF IMAGING SYSTEM

RELATED APPLICATION

This application claims the benefit of and priority to U.S. Provisional Application No. 61/739,881, filed Dec. 20, 2012, which is incorporated by reference in its entirety.

TECHNICAL FIELD

The invention generally relates to methods for manually calibrating Time-of-Flight based imaging systems and interferometric systems more particularly, such as optical coherence tomography systems.

BACKGROUND

Time-of-Flight imaging technologies in medicine and other fields involve measuring the time required for light to travel from a light sources to a target and back to a detector. Those measurements are used to provide high resolution images of the target. Time-of-Flight principles have applications in such diverse technologies as optical coherence tomography (OCT), gated viewing, positron emission tomography (PET), and radiotherapy. Beyond medical imaging, time-of-flight technologies are used in computer vision, robotics, art restoration, laser speed enforcement, and vision aids with security and military applications.

One problem that arises in many time-of-flight measurement technologies relates to calibration. Light that has been sent and received by an imaging component such as a lens or a catheter can be used to present an image of the target. But, where a reference point or zero point is not known a priori, the image does not necessarily contain calibration information relating to scale. Different approaches to calibrating these systems have included automatic computer processing algorithms as well as iterative user manipulation.

Known computer processing algorithms are limited. Typical approaches involve programming a computer to try to identify a reference point of a known dimension in the image. But where the known reference point appears among other images with similar shapes or is partially obscured and appears incompletely, computer processors are not adept at the induction required to determine the location or extent of the reference point.

Manual calibration is limited by the imprecision of human input and the time required for multiple iterations of spotting a calibration target and inputting information then zooming, centering, or focusing and repeating the steps. In, for example, the medical imaging context, the time involved is problematic because calibration often must occur while the patient is being examined. The imprecision is problematic for at least two reasons. First, the system must be calibrated precisely so that the imaging operation can be focused on the intended target (i.e., scanning at the desired depth in OCT). Also, tissue conditions such as tumors, plaque, or glaucoma must be measured precisely to monitor the progress of the condition.

SUMMARY

The invention generally provides systems and methods for manually calibrating an imaging system in which a user looks at an image of a target and indicates a point near a location of a reference point within the image. An image processing operation is employed to determine the precise location of the reference point. Thus, a user can identify the actual location of the reference point and a processing algorithm can give precision to the actual location. Where the reference point is, for example, a physical feature that gets imaged while the target is imaged, information about the expected location of that physical feature may be independently provided to the system. The system calculates a calibration value based on the expected and actual locations and adjusts to display an image at a known scale. Where the imaging system is operating live, it can take new images, providing them at the known scale. Where a user is reviewing stored images, the imaging system can adjust those stored images to provide them at a known scale. Because images are provided at a known scale, imaging systems can be focused on the intended target and the resulting images reveal dimensions of target subject matter. For example, in medical imaging, the dimensions of a feature within tissue can be measured to monitor the progress of a condition.

Systems and methods of the invention have particular utility in interferometric imaging applications where light from a reference path is combined with light from a sample path and the resulting interference pattern is analyzed. In OCT, for example, an interferometer is used to split light into fiber optic-based sample and reference paths. The length of the reference path must be adjusted to match the length of the sample path as defined by the outer surface of the imaging catheter sheath. The difference between the length of the sample and the reference path is the z-offset, which is zero when the paths have matched lengths. If the z-offset is known, the system can be calibrated by changing the length of the reference path to match the length of the sample path. This can be accomplished, for example, by operating a motor within a variable delay line (VDL) in the reference path. The invention provides methods for calibrating an interferometric imaging system by determining a z-offset of the system and using the determined z-offset value to provide an image at a known scale.

In certain aspects, the invention provides a method of calibrating an imaging system by displaying an image showing a target and a reference item, receiving user input indicating a point within the image, and detecting a location of the reference item within an area around the indicated point. If the reference is not detected within the area, the area may be expanded and the detection step repeated. The detected location is used to calculate a calibration value and a calibrated image of the target at a known scale is provided.

In some embodiments, the imaging system is an optical coherence tomography system. The reference item can be an image of a catheter sheath (e.g., a known surface such as the outer surface of the sheath). A scan from the system can be displayed, for example, on a computer monitor in tomographic view or in an image-longitudinal display. A user of the system can identify the catheter sheath and indicate its location by an input gesture, such as clicking with a mouse or touching a touchscreen. The reference item can be detected by a morphological image processing operation such as, for example, erosion, dilation, or a combination thereof. Where the imaging system is an intravascular OCT system, the catheter sheath may appear generally as a vertical lineal element in a B-scan.

A processor can begin by analyzing, for example, an area of the B-scan around a point corresponding to the user's input. Thus the user input is taken as a starting point, and image processing is performed to identify the reference item (catheter sheath) within the area around the point. Using signal processing operations, the processing system finds a line in the area, for example, the highest valued contiguous line. The processing system can extrapolate and expand a search or processing algorithm. For example, where the line is substantially vertical, the system looks up and down to identify a location of substantially all of the catheter sheath.

In some OCT operations, an imaging catheter is associated with a specific sample path length. Path length may be provided with each catheter, for example, by a manufacturer. The catheter sample path length can give an expected location of the reference point. Where the expected location is thus provided, a difference between the actual location and the expected location can be used to detect and correct for, for example, path length changes (e.g., stretching) during operation.

With a calibration value calculated, the imaging system can provide a calibrated image—either in live mode, by making a new scan, or in review mode, by transforming stored image data.

In related aspects, the invention provides an imaging system that includes a processor and a computer-readable storage medium having instructions therein which can be executed to cause the system to display an image showing a target and a reference item, receive user input indicating a point within the image, and detect a location of the reference item within an area around the indicated point. The system uses the detected location to calculate a calibration value and provide a calibrated image of the target at a known scale.

In other aspects, the invention provides a method of calibrating an imaging system by displaying an image showing a target and a reference item, receiving user input indicating a motion of the reference item within the image, and calculating a calibration value based on indicated motion of the reference item. For example, a user can use a mouse to drag an image of the reference item onto a calibration mark, as seen on a computer screen. The user input indicating a motion of the reference item can be a drag-and-drop operation performed with a computer pointing device (e.g., mouse or trackpad), a drag along a touchscreen, or any other suitable computer input method. The motion indicated by the input is used to calculate the calibration value. Based on the calculated calibration value, a scaled image of the target is provided.

Methods of the invention include transforming the reference item within the image by, for example, re-sizing, rotation, translating, or a combination thereof. In some embodiments, the system is an interferometric imaging system and the reference item is a portion of the system itself. For example, where the reference item is an image of an OCT catheter sheath, the dragging motion can indicate a z-offset calibration value, i.e., a change in a radius associated with a zero-point in the image. The z-offset calibration can be accomplished by moving a VDL motor or transforming image data.

In some embodiments, the user input is received, and then the calibration operation (e.g., moving the VDL or transforming an existing image) is performed. In certain embodiments, the calibration operation is performed while the user input is received. Thus the user experiences that they are changing the image. Where an OCT system is used, the user experiences dragging the catheter sheath inwards or outwards (for example, to a reference calibration mark) and thus changing the image.

In some related aspects, the invention provides an imaging system that includes a processor and a computer-readable storage medium having instructions therein which can be executed to cause the system to display an image showing a target and a reference item, receive user input indicating a motion of the reference item within the image, and calculate a calibration value based on indicated motion of the reference item. The calibration value is used to provide a scaled image of the target.

DETAILED DESCRIPTION

Figure 1:
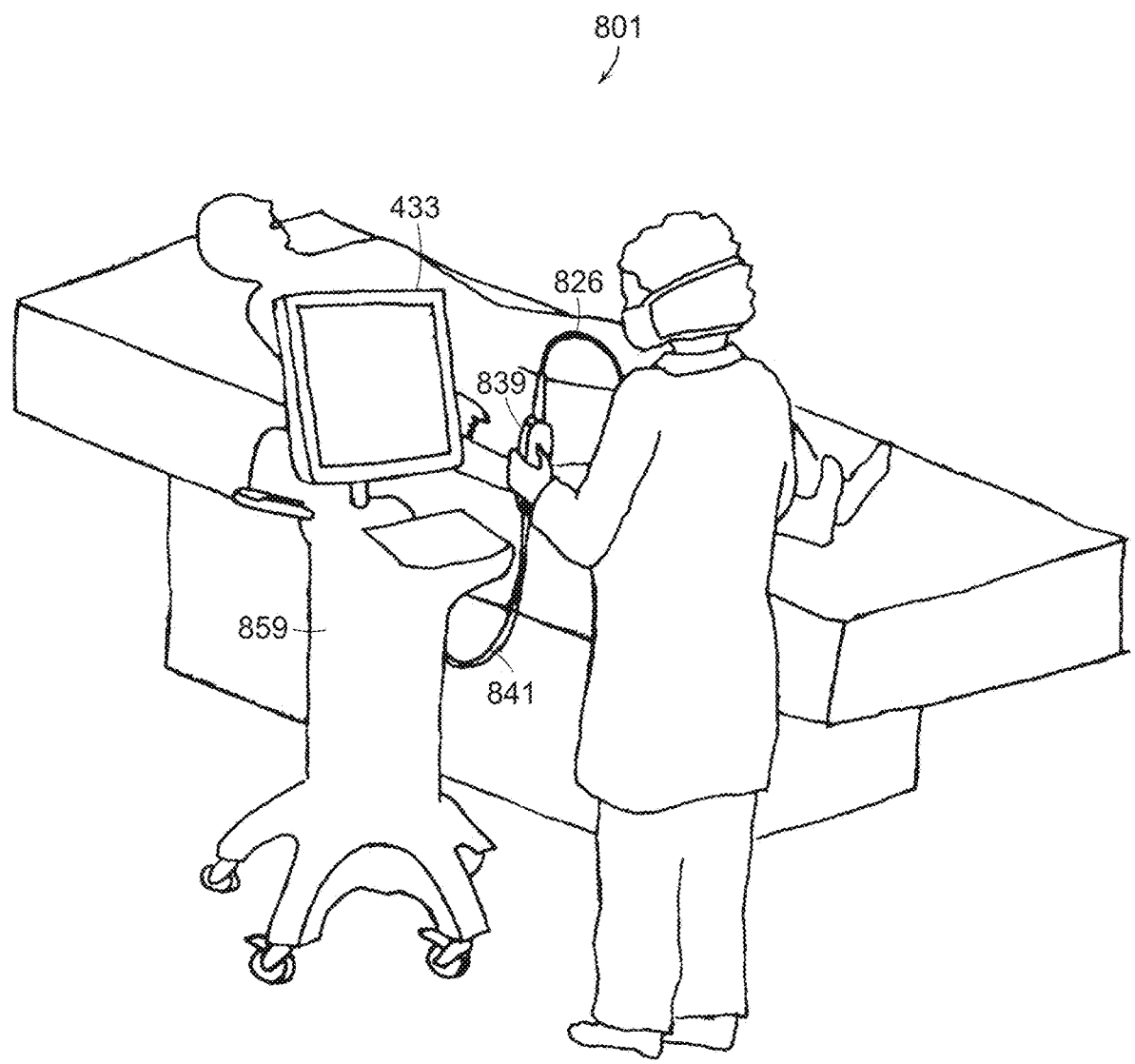
FIG. 1 shows use of an imaging system according to certain embodiments.

The invention provides systems and methods for calibrating an imaging system. Systems and methods of the invention have application in imaging systems that require calibration to provide a scale. Exemplary systems include imaging and sensing systems based on principles of time-of-flight or coherent interference. In some embodiments, systems and applications contemplated for use with the invention include optical coherence tomography (OCT), time-of-flight cameras such as the CamCube 3.0 TOF camera sold under the trademark PDM[VISION] by PMDTechnologies GmbH (Siegen, Germany), or time-of-flight positron emission tomography (PET) technologies. See, e.g., Placht et al., 2012, Fast time-of-flight camera based surface registration for radiotherapy patient positioning, Med Phys 39:4-17; Karp et al., 2009, The benefit of time-of-flight in PET imaging, J Nucl Med 49:462-470. Other imaging systems for use with the invention include, for example, gated viewing, radiotherapy, intra-vascular ultrasound, magnetic resonance imaging, elastographic techniques such as magnetic resonance elastography or transient elastography systems such as FibroScan by Echosens (Paris, France), and electrical impedance tomography, as well as other applications in computer vision, robotics, art restoration, laser speed enforcement, and vision aids with security and military applications.

In OCT systems, a light source is used to provide a beam of coherent light. The light source can include an optical gain medium (e.g., laser or optical amplifier) to produce coherent light by stimulated emission. In some embodiments, the gain medium is provided by a semiconductor optical amplifier. A light source may further include other components, such as a tunable filter that allows a user to select a wavelength of light to be amplified. Wavelengths commonly used in medical applications include near-infrared light, for example between about 800 nm and about 1700 nm.

Generally, there are two types of OCT systems, common beam path systems and differential beam path systems, that differ from each other based upon the optical layout of the systems. A common beam path system sends all produced light through a single optical fiber to generate a reference signal and a sample signal whereas a differential beam path system splits the produced light such that a portion of the light is directed to the sample and the other portion is directed to a reference surface. Common beam path systems are further described for example in U.S. Pat. Nos. 7,999,938; 7,995,210; and 7,787,127 the contents of each of which are incorporated by reference herein in their entirety.

In a differential beam path system, the coherent light from the light source is input into an interferometer and split into a reference path and a sample path. The sample path is directed to the target and used to image the target. Reflections from the sample path are joined with the reference path and the combination of the reference-path light and the sample-path light produces interference patterns in the resulting light. The light, and thus the patterns, are converted to electric signals, which are then analyzed to produce depth-resolved images of the target tissue on a micron scale. Exemplary differential beam path interferometers are Mach-Zehnder interferometers and Michelson interferometers. Differential beam path interferometers are further described for example in U.S. Pat. Nos. 7,783,337; 6,134,003; and 6,421,164, the contents of each of which are incorporated by reference herein in its entirety.

Commercially available OCT systems are employed in diverse applications, including art conservation and diagnostic medicine, notably in ophthalmology where OCT can be used to obtain detailed images from within the retina. The detailed images of the retina allow one to identify diseases and trauma of the eye. Other applications of imaging systems of the invention include, for example, dermatology (e.g., to image subsurface structural and blood flow formations), dentistry (to image teeth and gum line), gastroenterology (e.g., to image the gastrointestinal tract to detect polyps and inflammation), and cancer diagnostics (for example, to discriminate between malignant and normal tissue).

In certain embodiments, systems and methods of the invention image within a lumen of tissue. Various lumen of biological structures may be imaged including, for example, blood vessels, including, but not limited to vasculature of the lymphatic and nervous systems, various structures of the gastrointestinal tract including lumen of the small intestine, large intestine, stomach, esophagus, colon, pancreatic duct, bile duct, hepatic duct, lumen of the reproductive tract including the vas deferens, vagina, uterus and fallopian tubes, structures of the urinary tract including urinary collecting ducts, renal tubules, ureter, and bladder, and structures of the head and neck and pulmonary system including sinuses, parotid, trachea, bronchi, and lungs. Systems and methods of the invention have particular applicability in imaging veins and arteries such as, for example, the arteries of the heart. Since an OCT system can be calibrated to provide scale information, intravascular OCT imaging of the coronary arteries can reveal plaque build-up over time, change in dimensions of features, and progress of thrombotic elements. The accumulation of plaque within the artery wall over decades is the setup for vulnerable plaque which, in turn, leads to heart attack and stenosis (narrowing) of the artery. OCT images, if scaled or calibrated, are useful in determining both plaque volume within the wall of the artery and/or the degree of stenosis of the artery lumen. Intravascular OCT can also be used to assess the effects of treatments of stenosis such as with hydraulic angioplasty expansion of the artery, with or without stents, and the results of medical therapy over time.

FIG. 1 depicts the use of an exemplary intravascular OCT system 801. A physician controls an imaging catheter 826 through use of a handheld patient interface module (PIM) 839 to collect image data from a patient. Image data collected through catheter 826 is transmitted by PIM cable 841 to an imaging engine 859, which can be, for example, housed within a bedside unit or in a nearby computer installation or in a server rack coupled via networking technologies. As shown in FIG. 1, an OCT system can further include a workstation 433 (e.g., a monitor, keyboard, and mouse).

Figure 2:
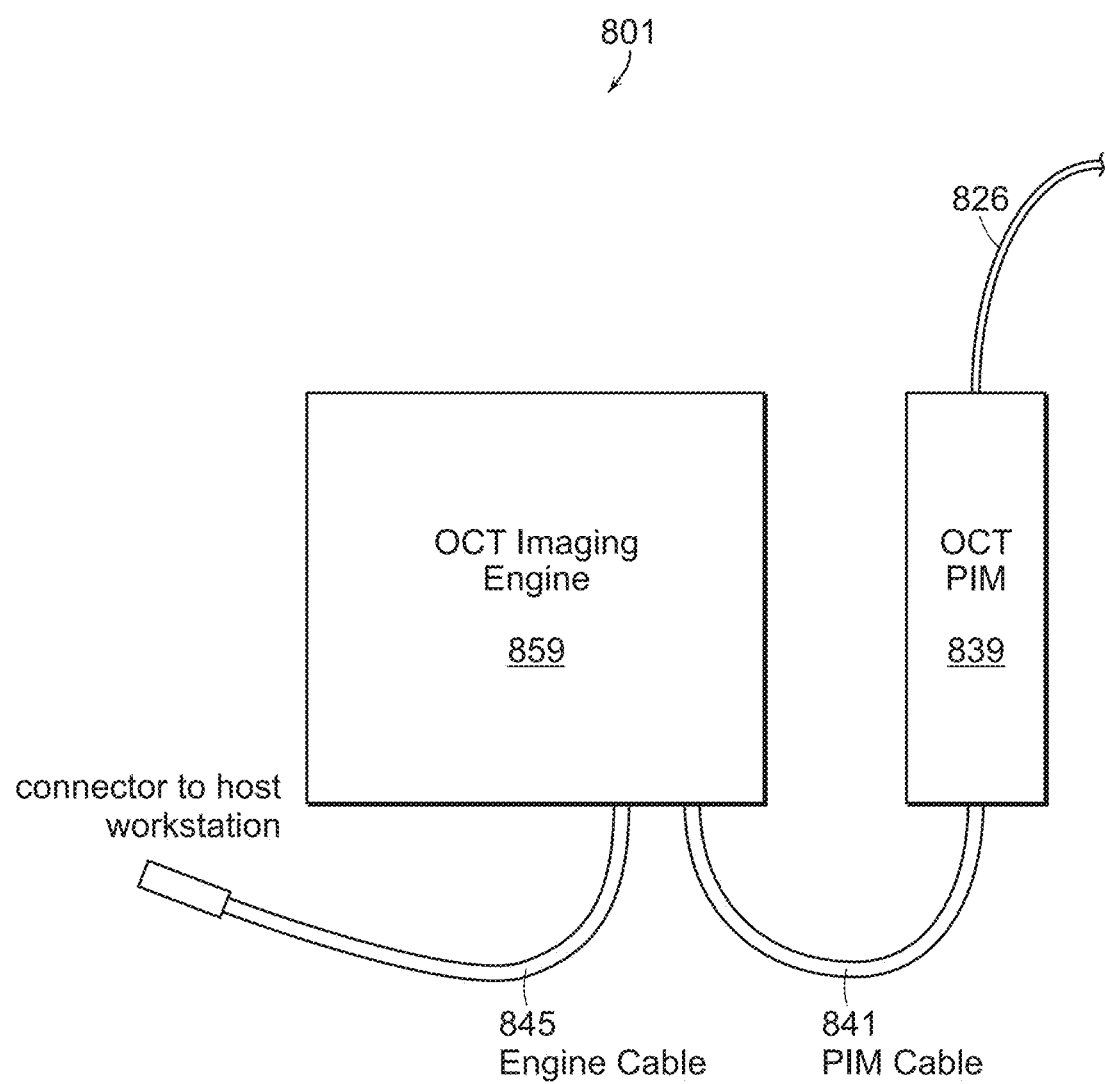
FIG. 2 is a diagram of components of an OCT system.

FIG. 2 gives a block diagram of components of OCT system 801. Imaging engine 859 is coupled to PIM 839 via PIM cable 841. Imaging catheter 826 extends from PIM 839 to the site of imaging. Engine cable 845 connects imaging engine 859 to host workstation 433. OCT is discussed in U.S. Pat. No. 8,108,030; U.S. Pub. 2011/0152771; U.S. Pub. 2010/0220334; U.S. Pub. 2009/0043191; U.S. Pub. 2008/0291463; and U.S. Pub. 2008/0180683, the contents of each of which are incorporated by reference in their entirety for all purposes. In certain embodiments, systems and methods of the invention include processing hardware configured to interact with more than one different three dimensional imaging system so that the tissue imaging devices and methods described here in can be alternatively used with OCT, IVUS, or other hardware.

As shown in FIG. 1, an operator controls imaging catheter 826 via handheld PIM 839. PIM 839 may include controls such as knobs or buttons to start or stop operation, set or vary speed or displacement, or otherwise control the imaging operation. PIM 839 further includes hardware for operating the imaging catheter.

Figure 3:
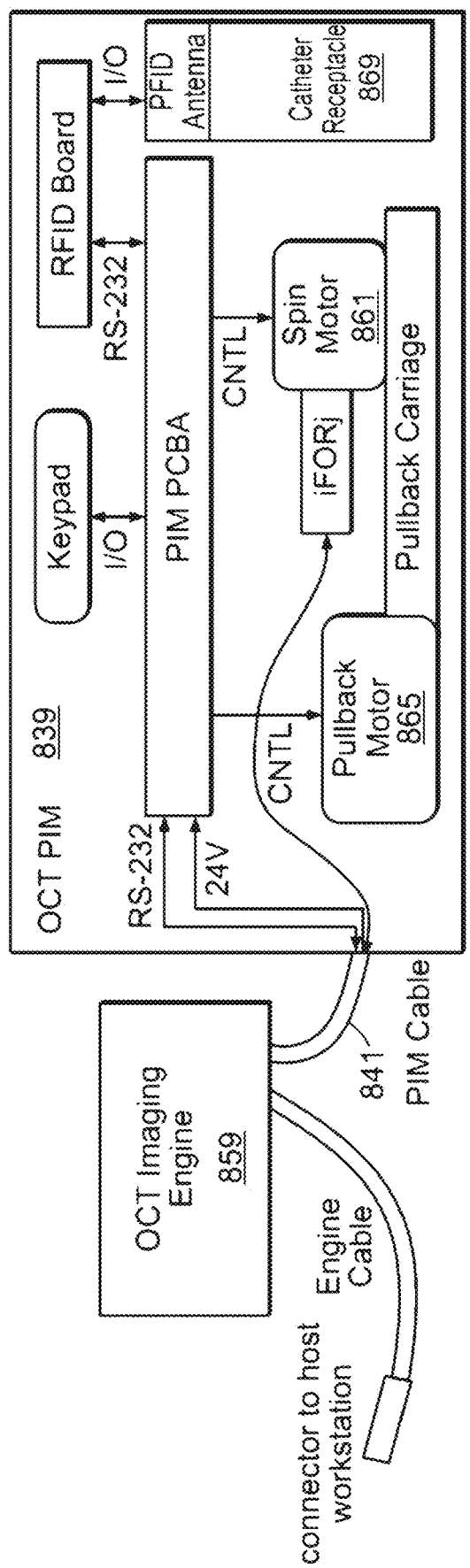
FIG. 3 diagrams components within a patient interface module (PIM).

FIG. 3 shows components of PIM 839. Catheter 826 is mounted to PIM 839 via a catheter receptacle 869. Spin motor 861 is provided to rotate catheter 826 and pullback motor 865 is provided to drive lateral translation of catheter 826. Also depicted is a keypad for input/output, a fiber-optic rotary joint (iFORj), a printed circuit board assembly (PCBA), and optional RFID components.

Figure 4:
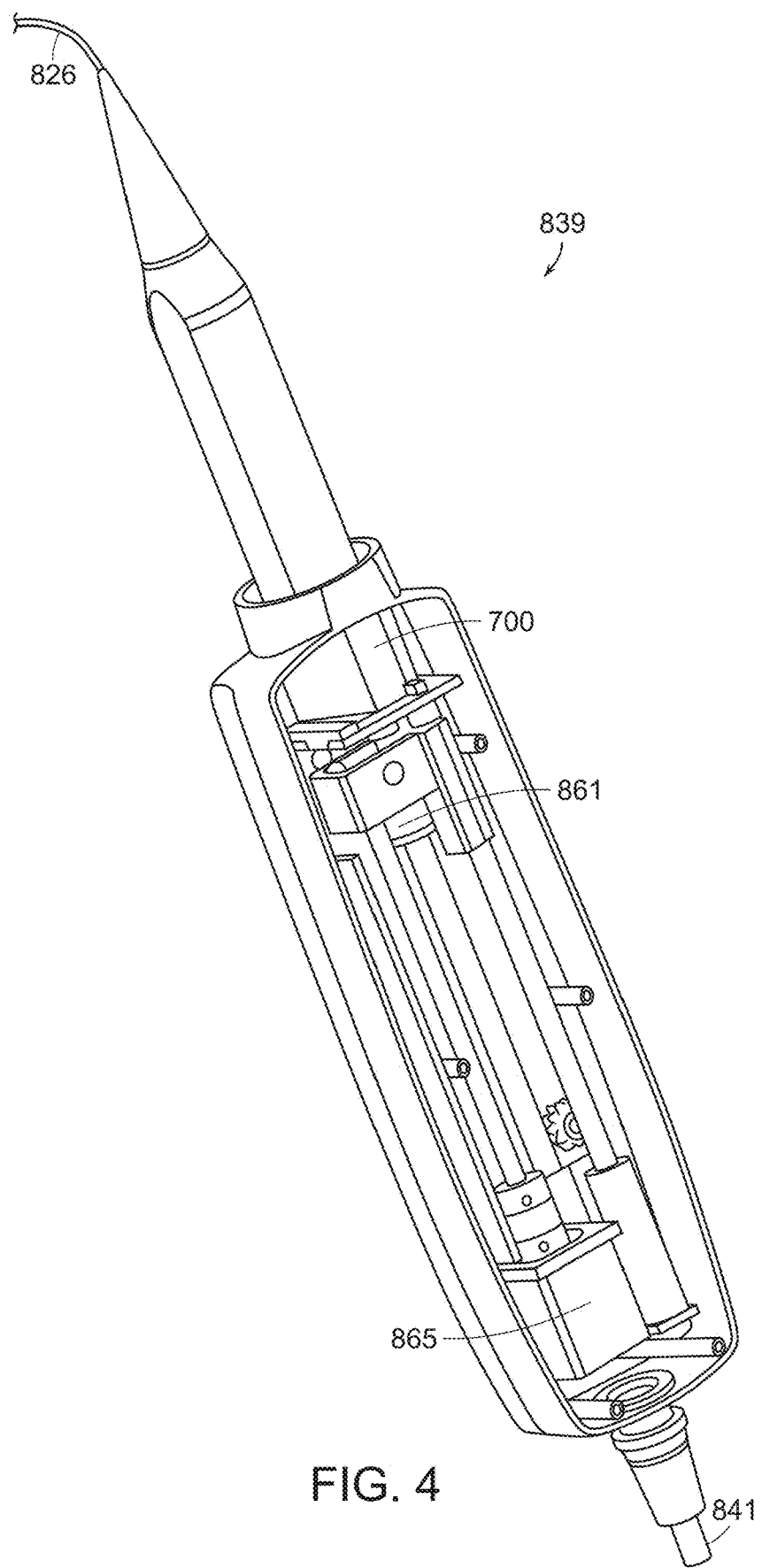
FIG. 4 shows the structure of a PIM according to certain embodiments.

FIG. 4 gives a perspective view of PIM 839 with a keypad cover removed. Spin motor 861 is provided to rotate catheter 826 and pullback motor 865 causes lateral translation. Optical signals, electrical signals, or both arrive at PIM 839 via PIM cable 841. PIM cable 841 extends to imaging engine 859 as shown in FIG. 2.

Figure 5:
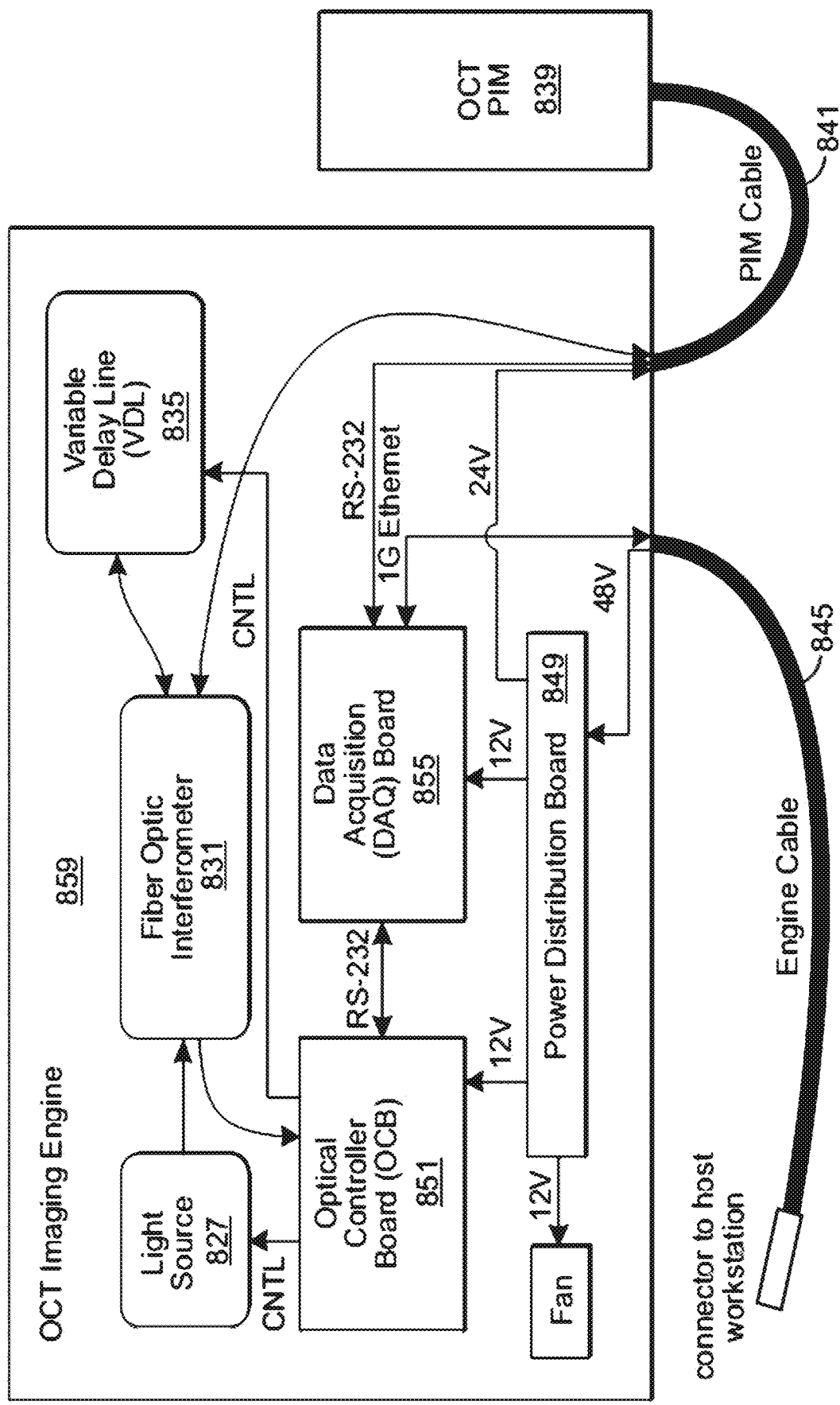
FIG. 5 is a diagram of components in an imaging engine.

FIG. 5 shows components of imaging engine 859. As shown in FIG. 5, the imaging engine 859 (e.g., a bedside unit) houses a power distribution board 849, light source 827, interferometer 831, and variable delay line 835 as well as a data acquisition (DAQ) board 855 and optical controller board (OCB) 851.

Light source 827, as discussed above, may use a laser or an optical amplifier as a source of coherent light. Coherent light is transmitted to interferometer 831.

Figure 6:
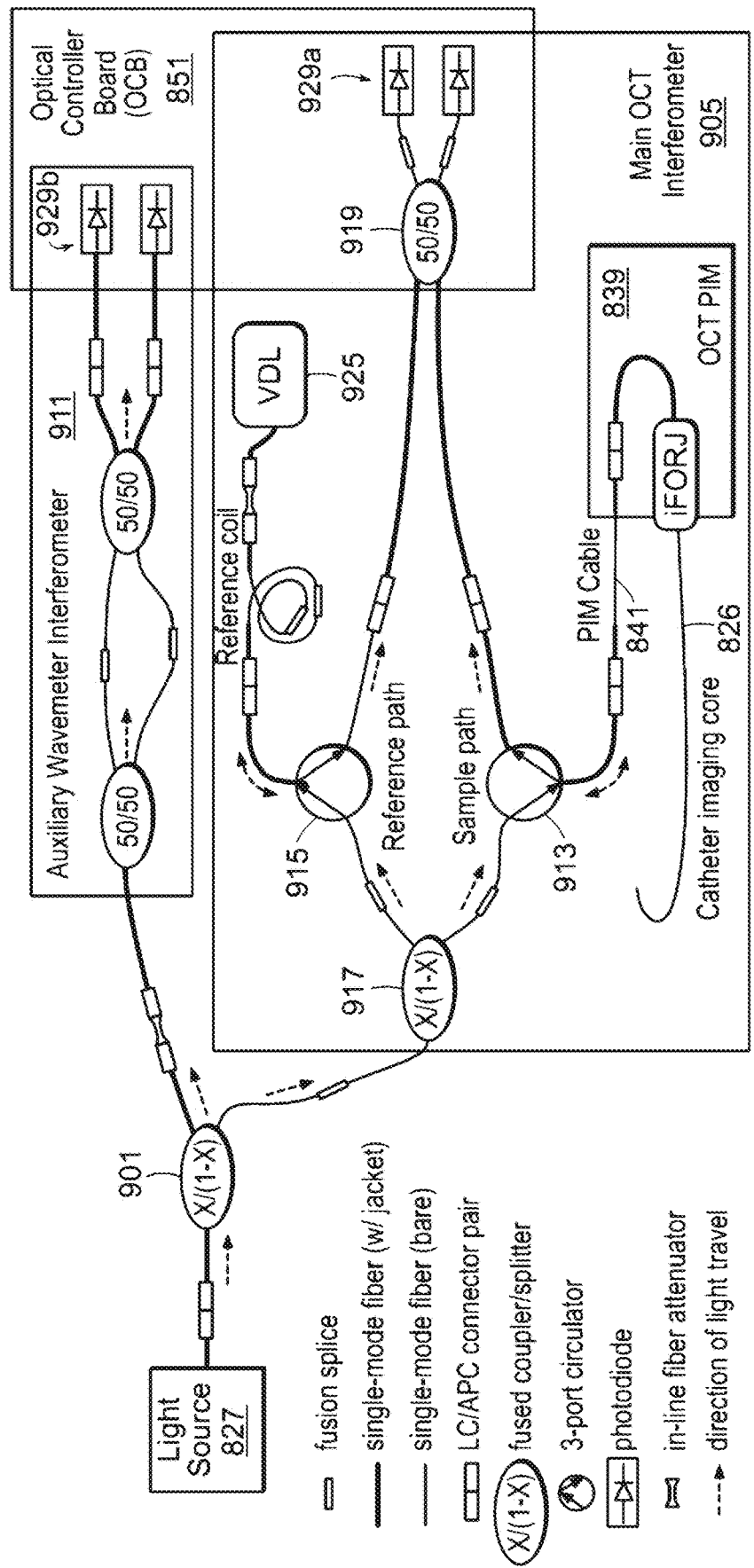
FIG. 6 is a diagram of an interferometer for use with systems of certain embodiments.

FIG. 6 shows a path of light through interferometer 831 during OCT imaging. Coherent light for image capture originates within the light source 827. This light is split between an OCT interferometer 905 and an auxiliary, or "clock", interferometer 911. Light directed to the OCT interferometer is further split by splitter 917 and recombined by splitter 919 with an asymmetric split ratio. The majority of the light is guided into the sample path 913 and the remainder into a reference path 915. The sample path includes optical fibers running through the PIM 839 and the imaging catheter 826 and terminating at the distal end of the imaging catheter where the image is captured.

An image is captured by introducing imaging catheter 826 into a target within a patient, such as a lumen of a blood vessel. This can be accomplished by using standard interventional techniques and tools such as a guide wire, guide catheter, or angiography system. Suitable imaging catheters and their use are discussed in U.S. Pat. Nos. 8,116,605 and 7,711,413, the contents of which are incorporated by reference in their entirety for all purposes.

Figure 7A:
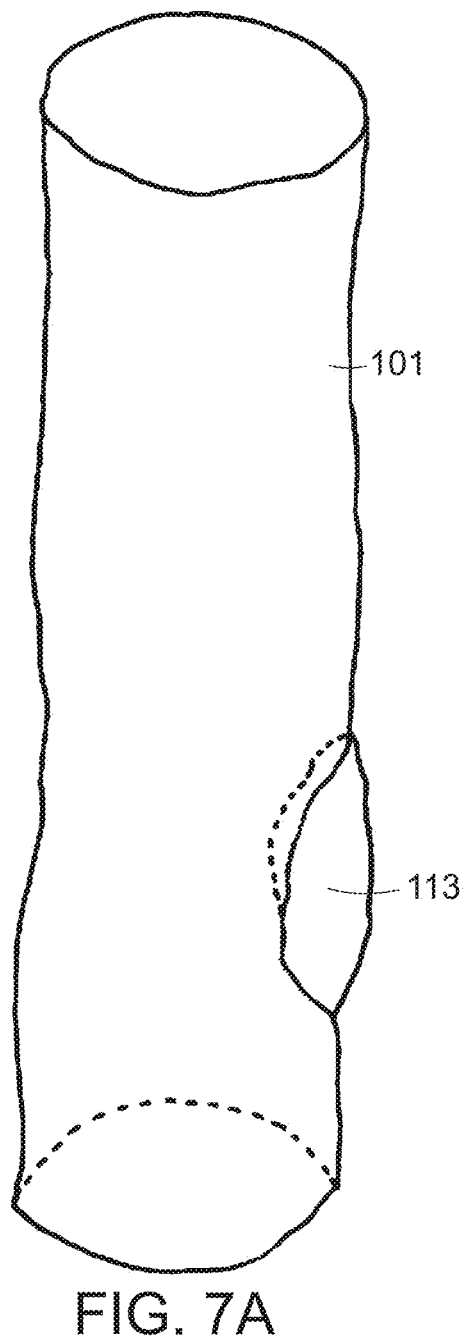
FIGS. 7A and 7B illustrate a segment of a blood vessel.
Figure 7B:
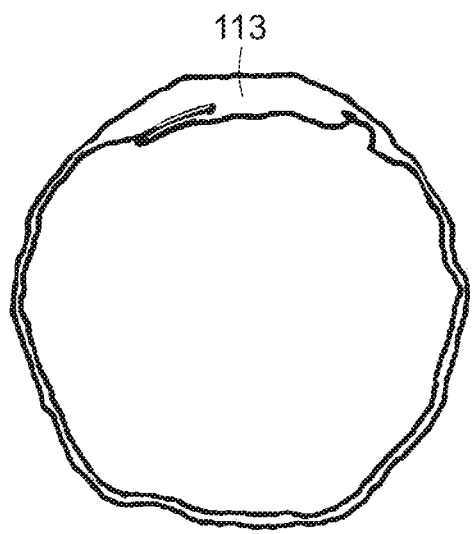

FIG. 7A provides an illustration of a segment of a vessel 101 having a feature 113 of interest. FIG. 7B shows a cross-section of vessel 101 through feature 113. In certain embodiments, intravascular imaging involves positioning imaging catheter 826 within vessel 101 near feature 113 and collecting data to provide a three-dimensional image. Data can be collected in three dimensions by rotating catheter 826 around a catheter axis to collect image data in radial directions around the catheter while also translating catheter 826 along the catheter axis. As a result of combined rotation and translation, catheter 826 collects image data from a series of scan lines (each referred to as an A-scan line, or A-scan) disposed in a helical array.

Figure 8:
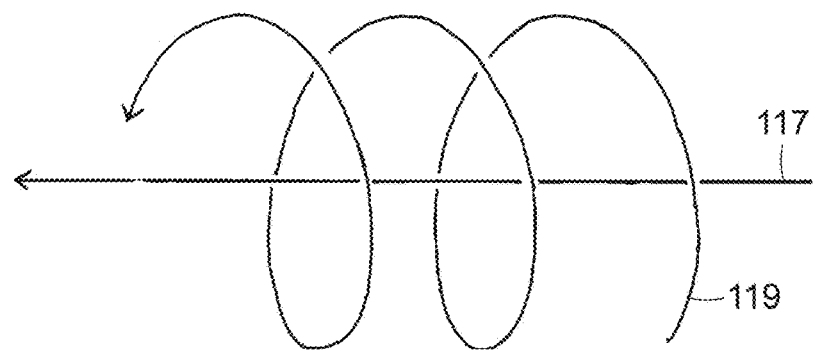
FIG. 8 shows the motion of parts of an imaging catheter according to certain embodiments of the invention.

FIG. 8 shows the motion of parts of an imaging catheter according to certain embodiments of the invention. Rotation of imaging catheter 826 around axis 117 is driven by spin motor 861 while translation along axis 117 is driven by pullback motor 865, as discussed above with reference to FIG. 4. An imaging tip of catheter 826 generally follows helical trace 119, resulting in a motion for image capture described by FIG. 8. Blood in the vessel is temporarily flushed with a clear solution for imaging. When operation is triggered from PIM 839 or a control console, the imaging core of catheter 826 rotates while collecting image data, which data is delivered to the imaging system.

Figure 9:
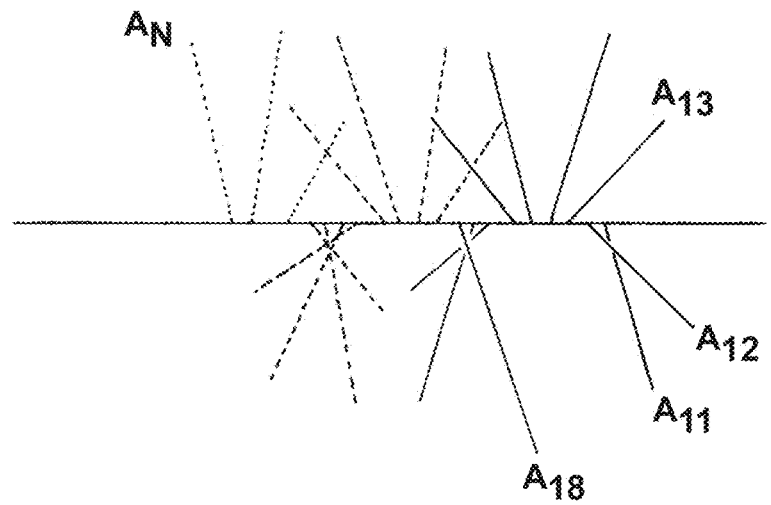
FIG. 9 shows an array of A scan lines of a three-dimensional imaging system according to certain embodiments of the invention.

FIG. 9 illustrates the helical array of A-scan lines $A_{11}$, $A_{12}$, . . . , $A_N$ captured by the imaging operation.

Figure 10:
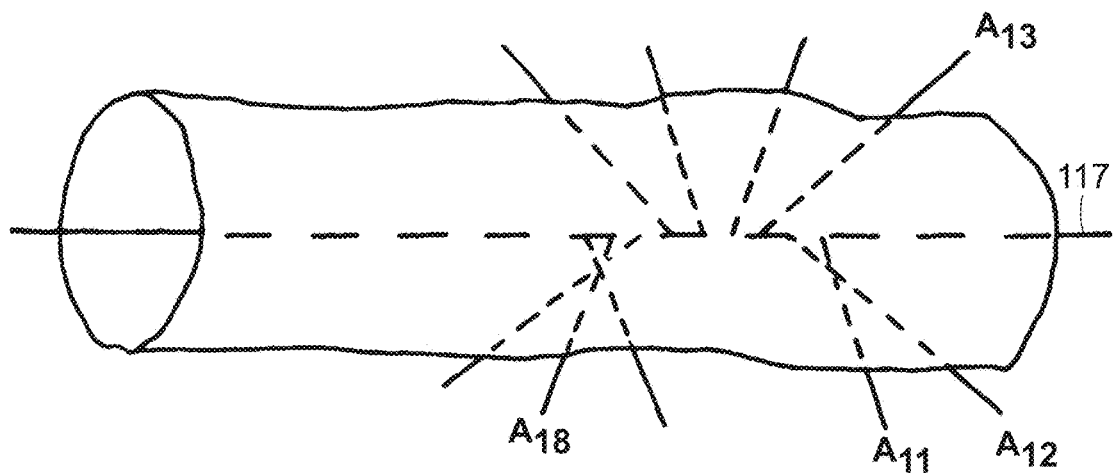
FIG. 10 shows the positioning of A scans with in a vessel.

FIG. 10 is provided to show the positioning of A-scans $A_{11}$, $A_{12}$, . . . , $A_N$ within vessel 101. Each place where one of A-scans $A_{11}$, $A_{12}$, . . . , $A_N$ intersects a surface of a feature within vessel 101 (e.g., a vessel wall) coherent light is reflected and detected. Catheter 826 translates along axis 117 being pushed or pulled by pullback motor 865.

Looking back at FIG. 6, the reflected, detected light is transmitted along sample path 913 to be recombined with the light from reference path 915 at splitter 919. Calibration of the system relates to a length of sample path 913 compared to a length of reference path 915. The difference between these lengths is referred to as the z-offset and when the paths are the same length, the z-offset is said to be zero, and the system is calibrated. Calibration will be discussed in more detail below. Z-offset is discussed in U.S. Pat. No. 8,116,605, the contents of which are hereby incorporated by reference in their entirety for all purposes. When the z-offset is zero, the system is said to be calibrated.

After combining light from the sample, and reference paths, the combined light from splitter 919 is split into orthogonal polarization states, resulting in RF-band polarization-diverse temporal interference fringe signals. The interference fringe signals are converted to photocurrents using PIN photodiodes $929a$, $929b$, . . . on the OCB 851 as shown in FIG. 6. The interfering, polarization splitting, and detection steps are done by a polarization diversity module (PDM) on the OCB. Signal from the OCB is sent to the DAQ 855, shown in FIG. 5. The DAQ includes a digital signal processing (DSP) microprocessor and a field programmable gate array (FPGA) to digitize signals and communicate with the host workstation and the PIM. The FPGA converts raw optical interference signals into meaningful OCT images. The DAQ also compresses data as necessary to reduce image transfer bandwidth to 1 gigabit per second (Gbps) (e.g., compressing frames with a lossy compression JPEG encoder).

Data is collected from A-scans $A_{11}$, $A_{12}$, . . . , $A_N$, as shown in FIG. 10, and stored in a tangible, non-transitory memory. A set of A-scans captured in a helical pattern during a rotation and pullback event can be collected and viewed alongside one another in a plane, in a format known as a B-scan.

Figure 11:
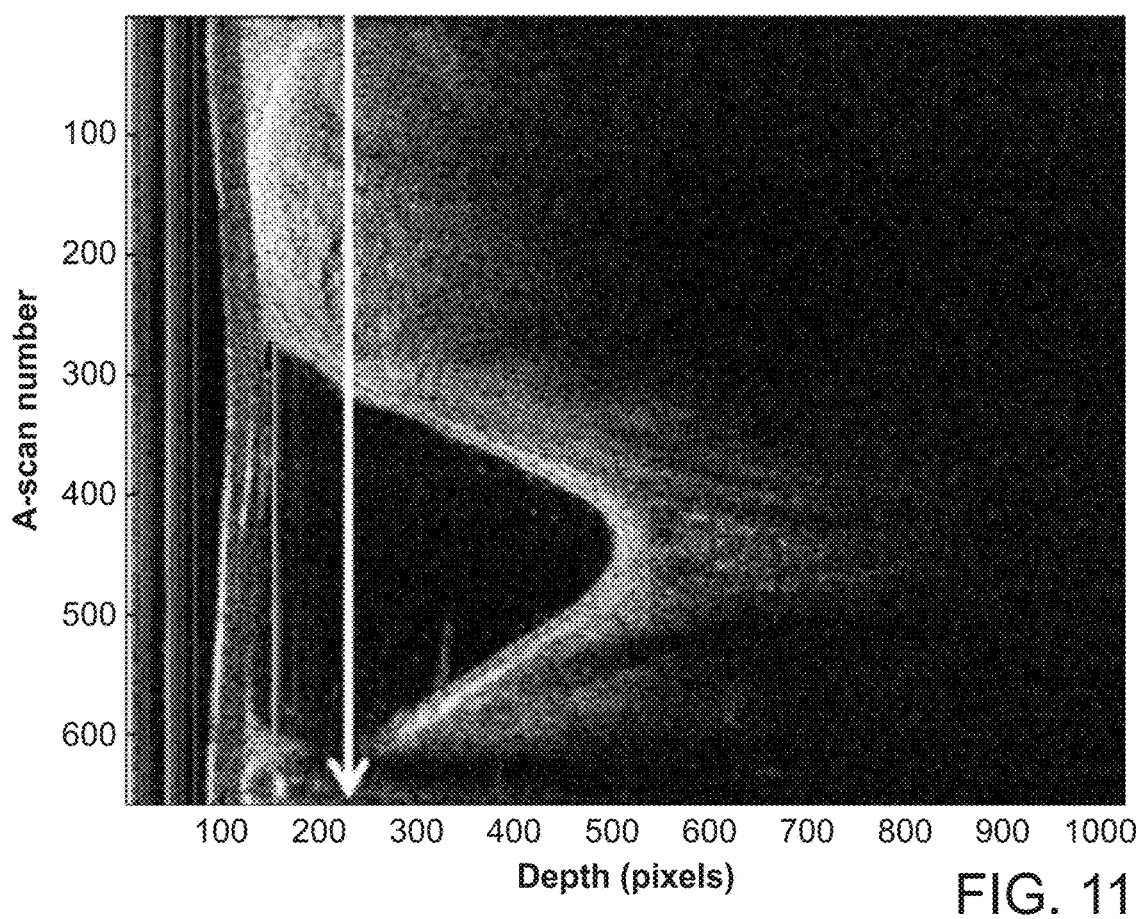
FIG. 11 shows a B-scan.

FIG. 11 gives a reproduction of a B-scan collected using an OCT system. Each horizontal row of pixels corresponds to one A-scan, with the first A-scan (e.g., $A_{11}$) being displayed across the top of the image. The horizontal axis labeled "Depth" represents a radial distance from imaging catheter 826. Noting—as shown in FIG. 9—that each A-scan line is progressively displaced from an adjacent A-scan in an angular direction around an axis 117 of catheter 826 (while also being displaced in a translational direction along axis 117), one set of A-scans associated with a 360° displacement around axis 117 can be collected into a view that depicts a slice of vessel 101 perpendicular to axis 117. This view is referred to as a tomographic view.

Figure 12:
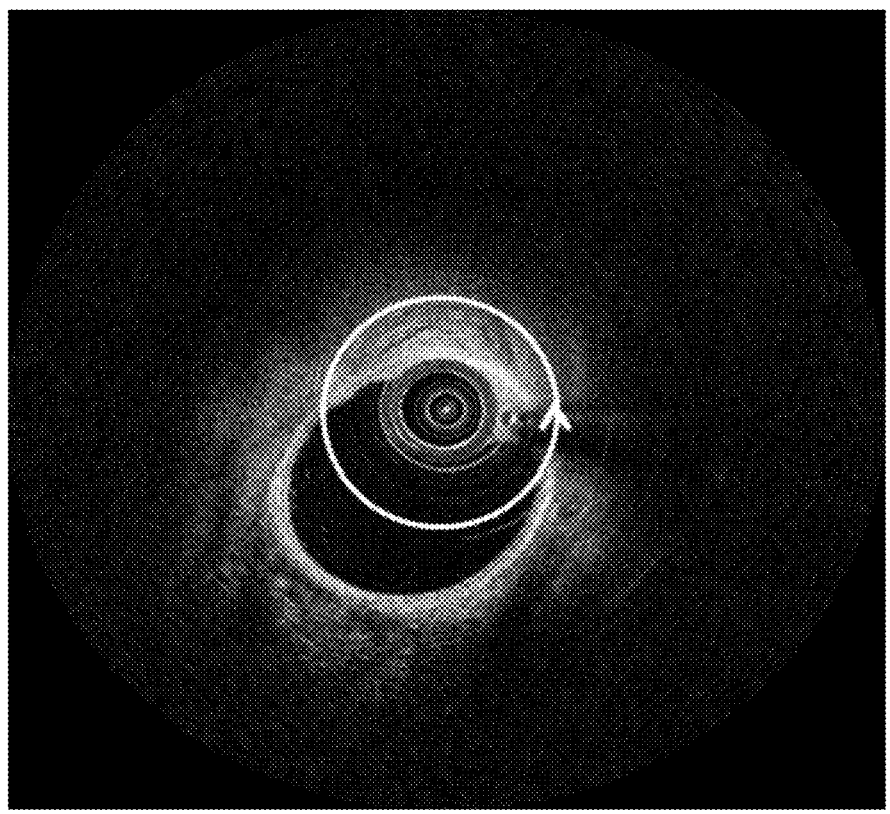
FIG. 12 shows a tomographic view based on the B-scan of FIG. 10.

FIG. 12 shows a tomographic view based on the B-scan of FIG. 10. A tomographic view comprises a set of A-scans that defines one circumference around vessel 101. An arrow pointing straight down in FIG. 11 corresponds to the circular arrow in FIG. 12 and aids in visualization of the three-dimensional nature of the data.

Figure 13:
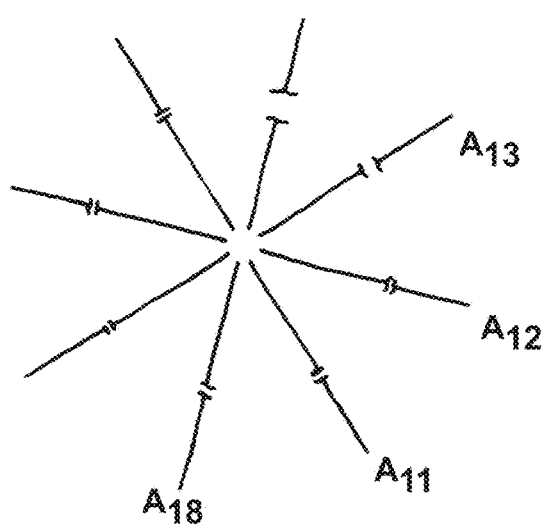
FIG. 13 illustrates a set of A scans used to compose a tomographic view.

FIG. 13 provides a cartoon illustration of a set of A-scans $A_{11}$, $A_{12}$, . . . , $A_{18}$ used to compose a tomographic view. These A-scan lines are shown as would be seen looking down axis 117 (i.e., longitudinal distance between them is not shown). While eight A-scan lines are here illustrated in cartoon format in FIG. 13, typical OCT applications can include between 300 and 1,000 A-scan lines to create a B scan (e.g., about 660) or a tomographic view.

Figure 14:
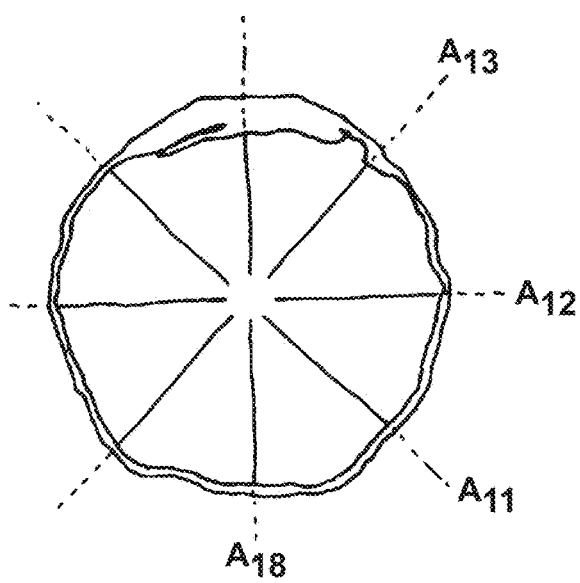
FIG. 14 shows the set of A scans shown in FIG. 13 within a cross section of a vessel.

FIG. 14 provides a cartoon illustration of the tomographic view associated with the A-scans of FIG. 13. Reflections detected along each A-scan line are associated with features within the imaged tissue. Reflected light from each A-scan is combined with corresponding light that was split and sent through reference path 915 and VDL 925 and interference between these two light paths as they are recombined indicates features in the tissue. Where a tomographic view such as is depicted in FIG. 14 generally represents an image as a planar view across a vessel (i.e., normal to axis 117), an image can also be represented as a planar view along a vessel (i.e., axis 117 lies in the plane of the view).

Figure 15:
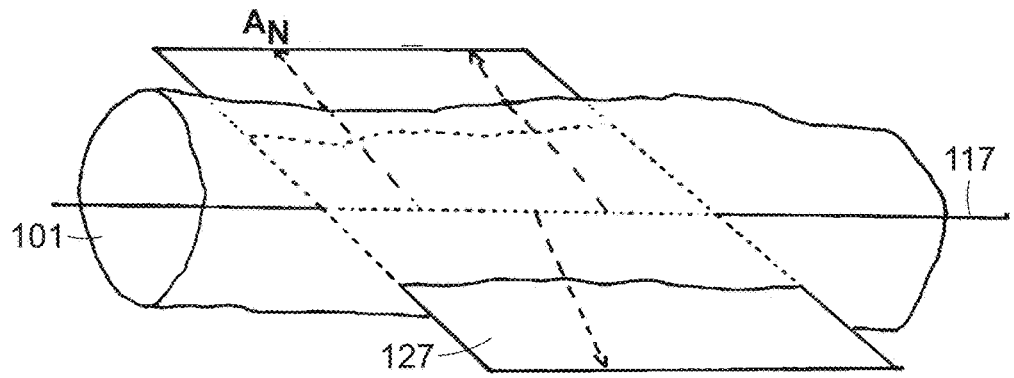
FIG. 15 shows a longitudinal plane through a vessel including several A scans.

FIG. 15 shows a longitudinal plane 127 through a vessel 101 including several A scans. Such a planar image along a vessel is sometimes referred to as an in-line digital view or image longitudinal display (ILD). As shown in FIG. 15, plane 127 generally comprises data associated with a subset of the A scans. The data of the A scan lines is processed according to systems and methods of the inventions to generate images of the tissue. By processing the data appropriately (e.g., by fast Fourier transformation), a two-dimensional image can be prepared from the three dimensional data set. Systems and methods of the invention provide one or more of a tomographic view, ILD, or both.

Figure 16:
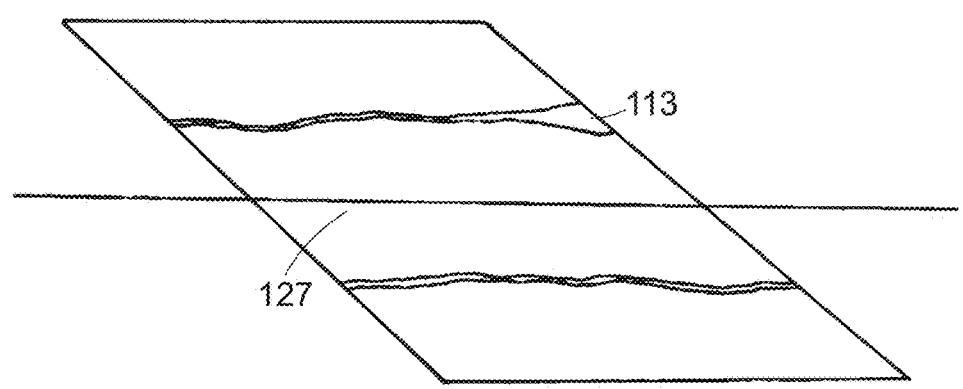
FIG. 16 is a perspective view of an image longitudinal display (ILD) in the same perspective as the longitudinal plane shown in FIG. 15.

FIG. 16 is a perspective view of an idealized plane shown including an exemplary ILD in the same perspective as the longitudinal plane shown in FIG. 15. Where an OCT system captures three-dimensional image data, host workstation 433 may store the three dimensional image data in a tangible, non-transitory memory and provides a display that includes a tomographic view (e.g., FIG. 14), an ILD (e.g., FIG. 16), or both (e.g., on a screen or computer monitor). In some embodiments, a tomographic view and an ILD are displayed together, providing information that operators can intuitively visualize as representing a three-dimensional structure.

Figure 17:
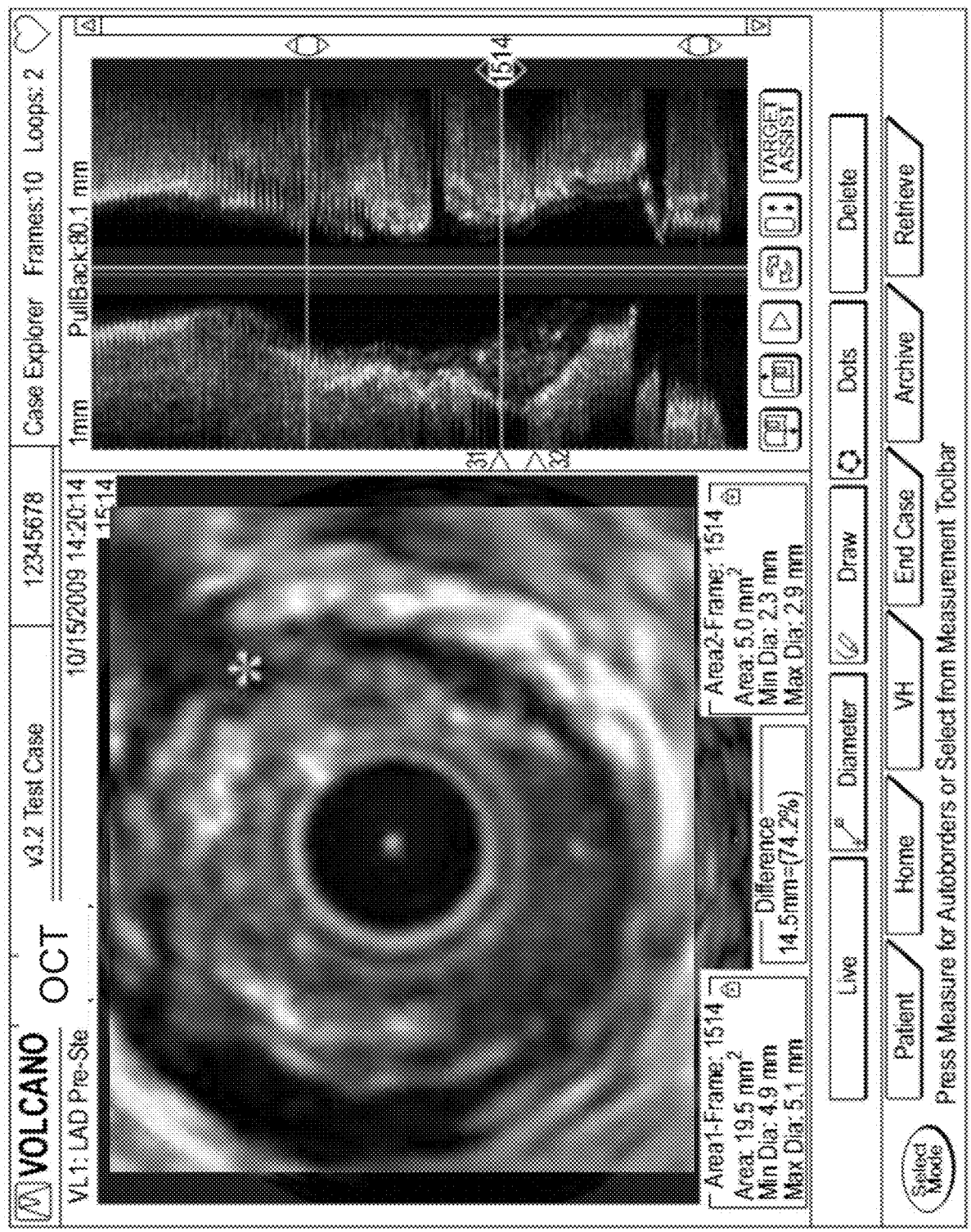
FIG. 17 shows a display of a system of the invention.

FIG. 17 is a reproduction of a display of an OCT system including a tomographic view on the left and an ILD on the right. As shown in FIG. 17, a tomographic view may include ring-like elements near the center and the ILD may include corresponding sets of vertical line-like elements. One ring in the tomographic view may correspond to one pair of lines in the ILD. These elements within the displays are often, in-fact, images of part of the imaging system itself. In some embodiments, a ring in a tomographic view and lines in an ILD represent a surface of catheter 826 such as, for example, an outer surface of a catheter sheath. The portions of the images extending away from those elements are the images of the patient's tissue.

In some embodiments, an OCT system is operated with interchangeable, replaceable, or single-use catheters. Each catheter 826 may provide a different length to sample path 913. For example, catheters may be used that are designed to be of different lengths, like-manufactured catheters may be subject to imperfect manufacturing tolerances, or catheters may stretch during use. However, to provide a calibrated or scaled image, the z-offset must be known (for post-imaging processing) or set to zero. A z-offset can be known directly (e.g., numerically) or can be known by reviewing an image and determining an apparent difference in an actual location of an element within the image and an expected location of the element within the image.

In some embodiments, the z-offset is calibrated by inspecting an image being captured while they system is running in live mode, and adjusting the actual length of reference path 915 to match the length of sample path 913.

VDL 925 on reference path 915 uses an adjustable fiber coil to match the length of reference path 915 to the length of sample path 913. The length of reference path 915 is adjusted by a stepper motor translating a mirror on a translation stage under the control of firmware or software. The free-space optical beam on the inside of the VDL 925 experiences more delay as the mirror moves away from the fixed input/output fiber. As VDL 925 is adjusted, a length of reference path 915 is known (based, for example, on manufactured specifications of the system).

In some embodiments, the known length of reference path 915 is used to display a calibration mark on a display. If the calibration mark is displayed at a position corresponding to a distal point on reference path 915, and if sample path 913 is the same length as reference path 915 (e.g., when z-offset is zero), it may be expected that a ring in a tomographic view that represents an outer surface of a catheter sheath will lie along the calibration mark.

When a display includes a calibration mark and a ring-like element representing an outer surface of the catheter sheath separated from one another, an operator has a visual indication that the display is not calibrated.

Figure 18:
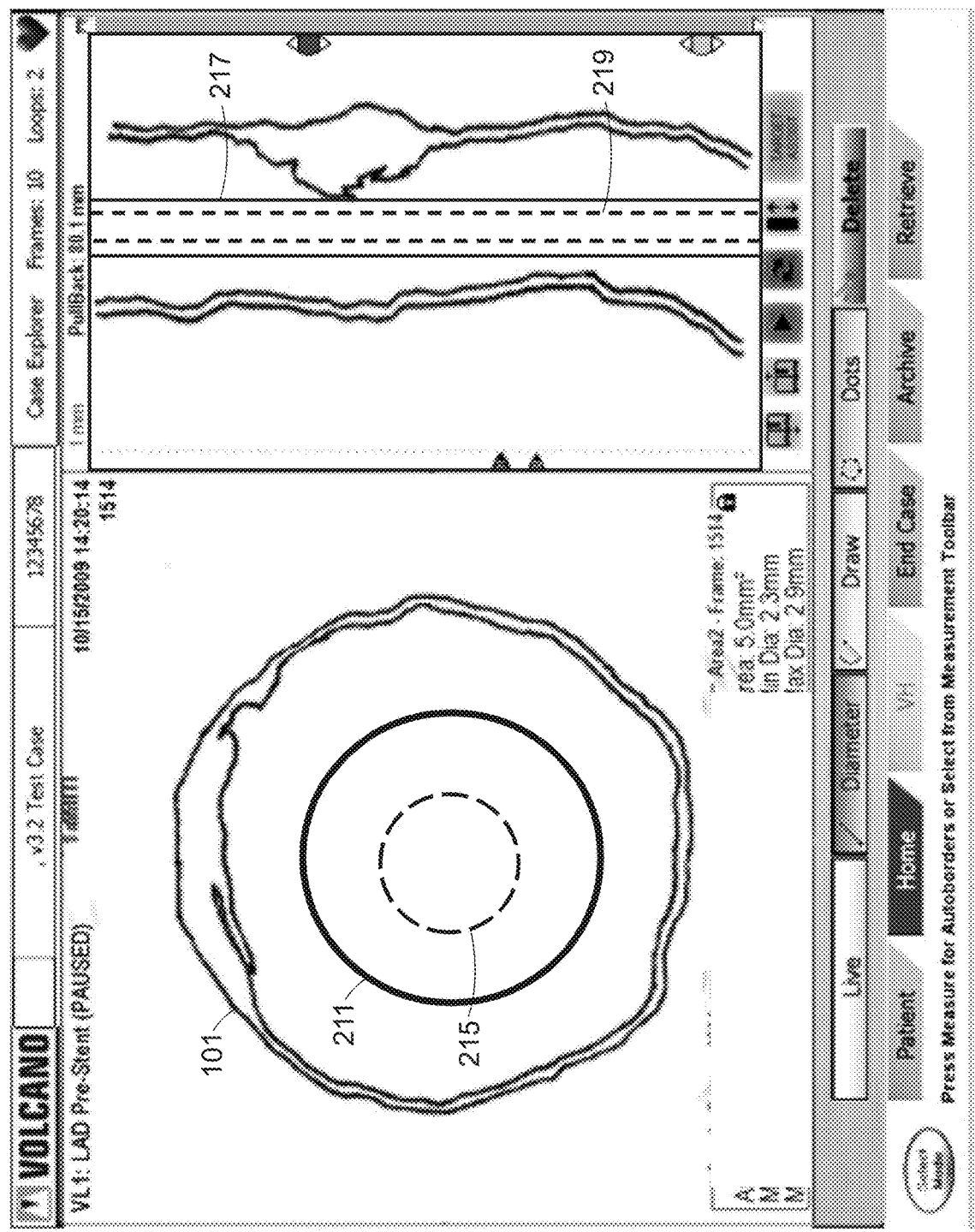
FIG. 18 is a display providing an image of the vessel shown in FIGS. 7A and 7B.

FIG. 18 is a cartoon illustration of a display 237 including an image of the vessel shown in FIGS. 7A and 7B, as rendered by a system of the invention. The images included in display 237 in FIG. 18 are rendered in a simplified style of the purposes of ease of understanding. A system of the invention may render a display as shown in FIG. 17, or in any style known in the art (e.g., with or without color).

As shown in FIG. 18, a tomographic view of vessel 101 is depicted alongside an ILD. An outer surface of a catheter sheath appears as a ring 211 in the tomographic view and as lines 217 in the ILD. The tomographic view is depicted as including calibration mark 215, while calibration mark 219 appears in the ILD.

In some embodiments, z-offset calibration involves precisely determining the position of ring 211 (or lines 217) in display 237 so that the system can calculate a z-offset based on a known position of calibration mark 215. Systems of the invention can determine the position of ring 211 or any other calibration element based on user input and an image processing operation. Any suitable user input can be used. In some embodiments discussed below, user input is a "click and drag" operation to move ring 211 to a calibration mark. In certain embodiments, user input is accepted in the form of a single click, a single touch of a touch screen, or some other simple gesture.

Figure 19:
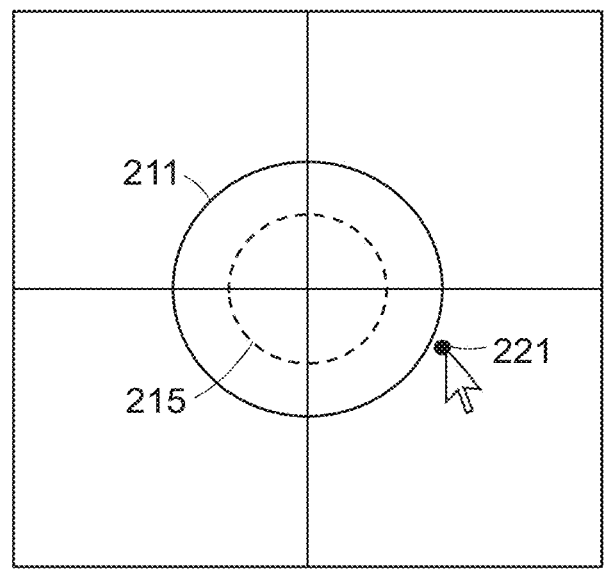
FIG. 19 illustrates receiving user input indicating a point within an image.

FIG. 19 illustrates, in simplified fashion, a display of an imaging system showing a catheter sheath 211 and calibration mark 215. A user can click on the display near the sheath 211. In some embodiments, the system detects the location of the catheter sheath with no more input from a user than an indication of a single point. A single point can be input by a mouse-click, a touch on a touchscreen, a light pen or light gun, by "driving" a point to a certain position with arrow keys or a joystick, or by any other suitable method known in the art.

The system can additionally use a processor to perform an image processing operation to detect sheath 211. In some embodiments, user input indicates a single point 221 on the screen. The system then defines an area around point 221.

Figure 20:
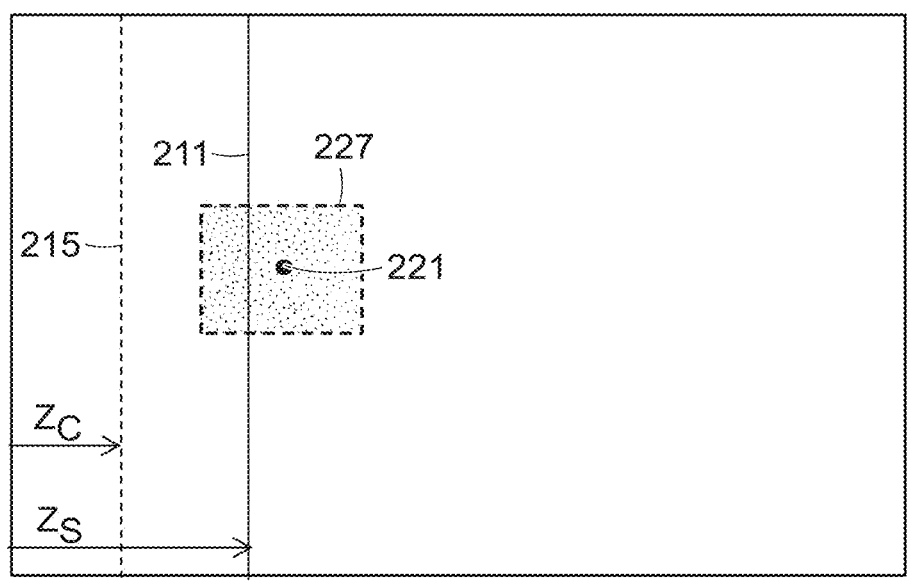
FIG. 20 shows an area around a point to be searched.

FIG. 20 depicts a defined area 227 around point 221 on a B-scan. Area 227 operates as a search window. The search window area 227 may be a rectangle, circle, ellipse, polygon, or other shape. It may have a predetermined area (e.g., a certain number of pixels). In some embodiments, a size and shape of area 227 is determined by a combination of input device resolution, screen area subtended by a pixel at the particular polar coordinates, current zoom factor, usability studies, or a combination thereof. Usability studies can be performed to establish a statistical model of user repeatability and reproducibility under controlled conditions.

The system searches for the sheath within area 227 by performing a processing operation on the corresponding data. The processing operation can be any suitable search algorithm known in the art.

In some embodiments, a morphological image processing operation is used. Morphological image processing includes operations such as erosion, dilation, opening, and closing, as well as combination thereof. In some embodiments, these operations involve converting the image data to binary data giving each pixel a binary value. With pixels within area 227 converted to binary, each pixel of catheter sheath 211 will be black, and the background pixels will predominantly be white. In erosion, every pixel that is touching background is changed into a background pixel. In dilation, every background pixel that is adjacent to the non-background object pixels is changed into an object pixel. Opening is an erosion followed by a dilation, and closing is a dilation followed by an erosion. Morphological image processing is discussed in Smith, The Scientist and Engineer's Guide to Digital Signal Processing, 1997, California Technical Publishing, San Diego, Calif., pp. 436-442.

If sheath 211 is not found within area 227, area 227 can be increased and the increased area can be searched. This strategy can exploit the statistical properties of signal-to-noise ratio (SNR) by which the ability to detect an object is proportional to the square root of its area. See Smith, Ibid., pp. 432-436.

With continued reference to FIG. 20, once a portion of catheter sheath 211 is detected within area 227, the search can then be extended "upwards" and "downwards" into adjacent A-scan lines in the B-scan until the entire catheter sheath 211 is detected by the processor and its location is determined with precision. In some embodiments, image processing operations incorporate algorithms with pre-set or user-set parameters that optimize results and continuity of results. For example, if a line appears that is not contiguous across an entire 100% of the image (e.g., the entire extent of the B-scan or a full circle in a tomographic view), an accept or reject parameter can be established based on a percent contiguous factor. In some embodiments, lines that are contiguous across less than 75% (or 50% or 90%, depending on applications) are rejected while others are accepted.

While described above as detecting a reference item (e.g., catheter sheath 211) by receiving user input followed by using a processor to detect a location of the sheath, the steps can be performed in other orders. For example, the system can apply morphological processing operations to an entire image and detect every element, or every element that satisfies a certain quality criterion. Then the system can receive user input that indicates a point within an image and the user can then choose the pre-detected element that is closest to that point within the image. Similarly, the steps can be performed simultaneously.

Using the methodologies herein, systems of the invention can detect an element within an image of an imaging system, such as an OCT system, with great precision, based on human input that need not be precise and computer processing that need not on its own be accurate. Based on this detection, an actual location of a catheter sheath is determined and thus a precise z-coordinate $Z_s$ for the catheter sheath (e.g., within a B-scan) is known. Where an expected z-coordinate $Z_c$ for the catheter sheath is known, based on information provided extrinsically, the z-offset, and thus a calibration value, can be determined. For example, in FIG. 20, $Z_s$ is depicted as lying to the right of $Z_c$, thereby showing a non-zero z-offset. The calibration value is then used to provide a calibrated image, or an image at a known scale.

In some embodiments, the system calculates or uses the mean, median, or root-mean-squared distance of the sheath from the calibration mark to compute the calibration value. This may be advantageous in the event of interfering speckle noise, rough or acylindrical sheaths, non-uniform catheter rotation (NURD), angular displacement of a transducer within the sheath, off-center positioning of the transducer within the sheath, or a combination thereof. In certain embodiments, only a subset of the detected points are used, for example, for efficiency or performance optimization.

Figure 21:
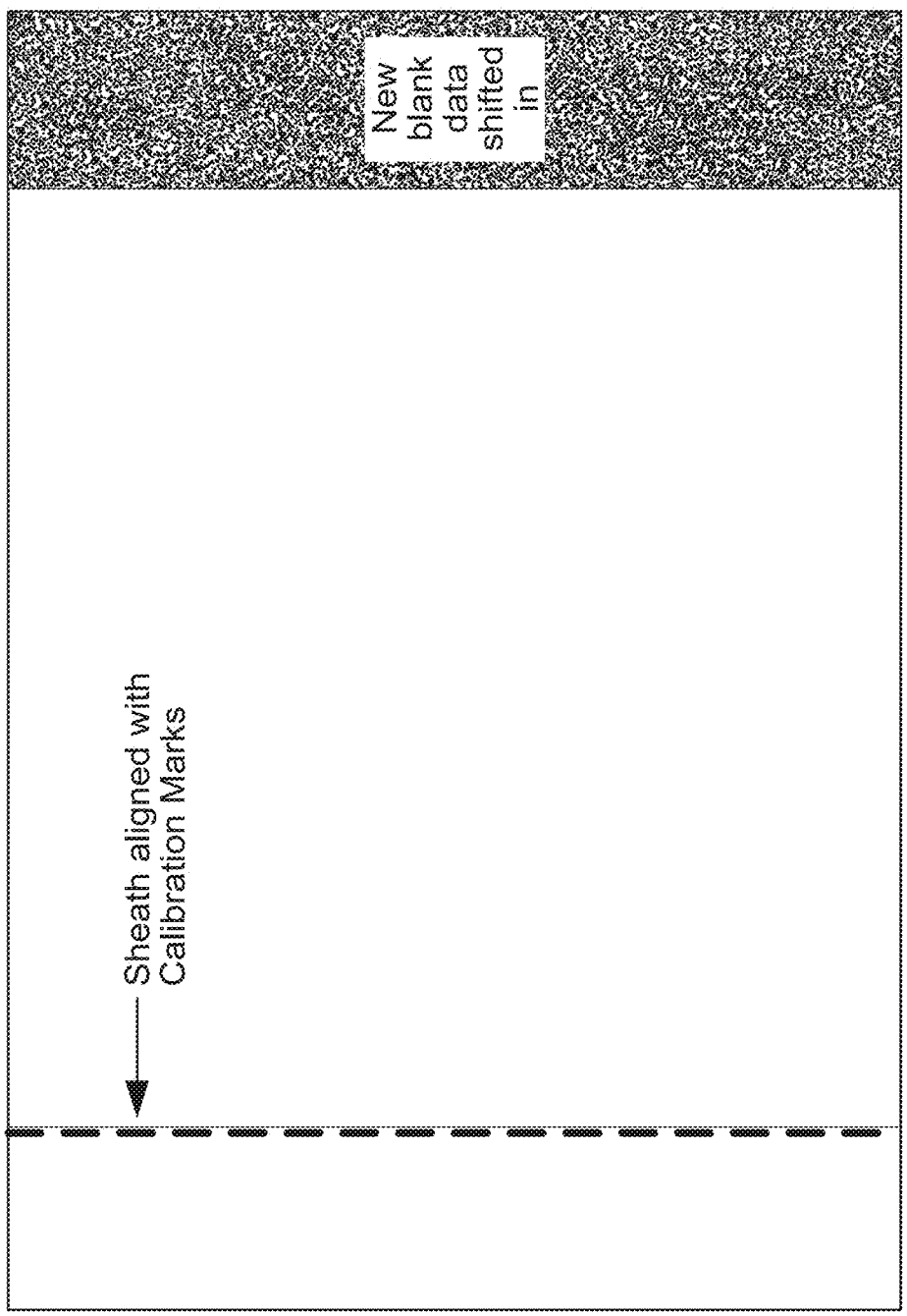
FIG. 21 shows a calibrated B-scan.

FIG. 21 shows a calibrated image, here, a B-scan. The image is depicted having the catheter sheath aligned with the calibration mark. Bars on the left and right side of FIG. 21 show that some data may be shifted out and some blank space introduced by the calibration. In an alternative embodiment, the image can be stretched or compressed, or a combination of stretching and shifting may be performed, depending on preferences, purposes, or functions of a system.

It will be appreciated that the foregoing description is applicable in live mode or review mode. If the imaging system is operating in live mode, capturing an image of tissue, the calibration can be put into effect either by changing the length of reference path 915 so that z-offset is zero or by transforming the dataset or on-screen image. The length of reference path 915 can be changed through the operation of the motor in the VDL. The distance $Z_c$-$Z_s$ is converted into millimeters and the a command is sent to move the VDL to a new position.

If the dataset is to be transformed, either in live mode or while the system is operating in review mode, the system is digitally shifted, stretched, or a combination thereof.

In another aspect, the invention provides a method for calibrating an imaging system based on receipt of user input that indicates a "motion", such as a click-and-drag operation on a computer screen.

Figure 22:
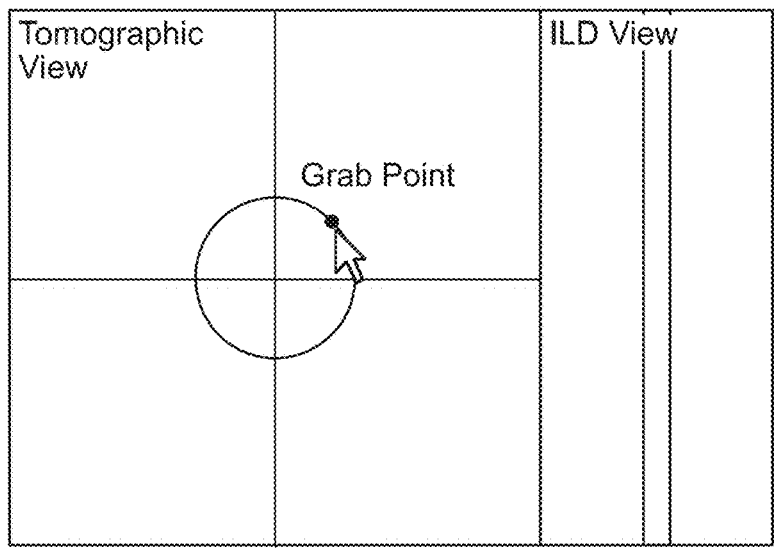
FIGS. 22 and 23 illustrates receiving user input indicating a motion
Figure 23:
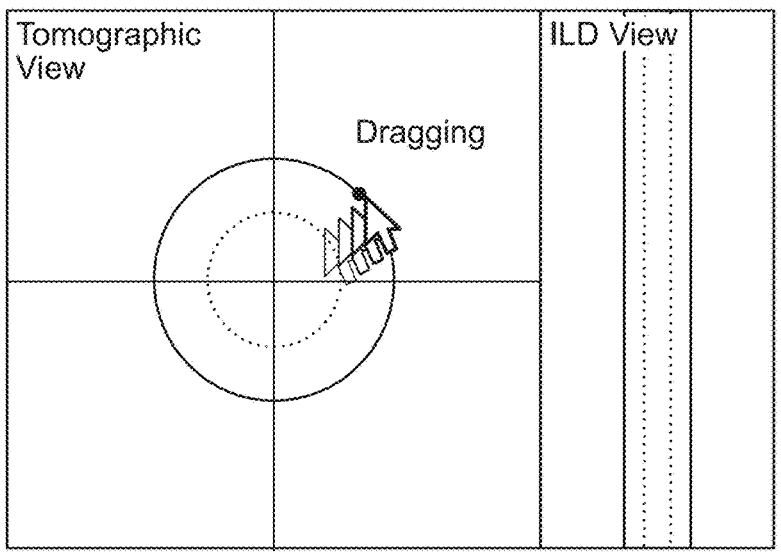

FIGS. 22 and 23 illustrate receiving user input indicating a motion through a mouse dragging operation. User input could also be a drag on a touchscreen or other input (arrow keys, pointer, trackball, etc.) As depicted in FIGS. 22-23, a user clicks on a reference item (e.g., sheath 211) with a mouse and drags it to a new position, for example, onto a calibration mark or other position on the display. The system (e.g., using a processor) can then calculate a calibration value based on indicated motion of the reference item.

This method allows a user to manually calibrate or apply any offset using a drag-and-drop operation on the tomographic view or on the ILD. While dragging, the distance between the grab point and current point represented by the tip of the mouse pointer (or analogous finger-touch point in touchscreens) may be continuously calculated. In live mode, the image may be shifted digitally or by moving the VDL and in review mode the image is transformed digitally, as discussed above.

Figure 24:
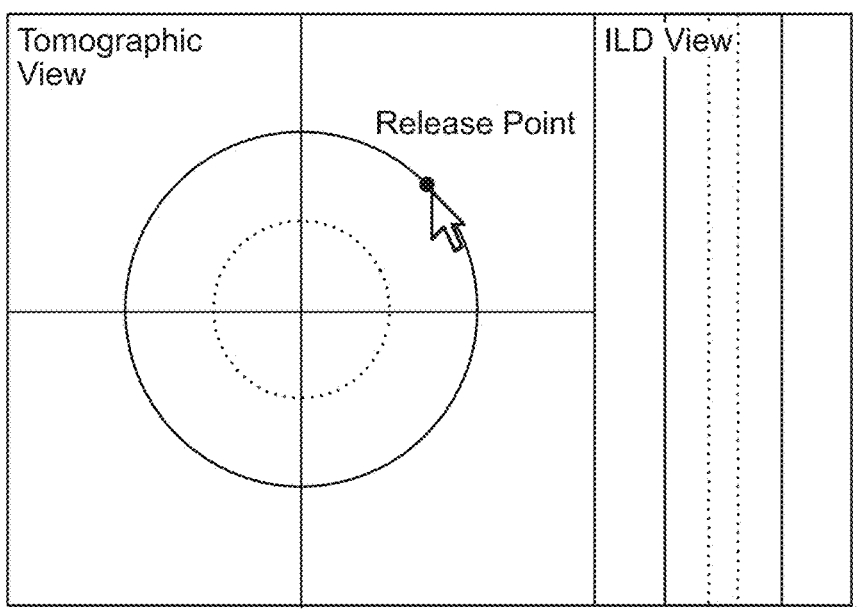
FIG. 24 illustrates providing a scaled image based on an indicated motion.

FIG. 24 shows releasing a click-and-drag motion. In some embodiments, the image is shifted (digitally or by moving the VDL) simultaneously with the user's drag motion. In certain embodiments, the system begins the shift after the user completes the drag input motion. (Note that in FIGS. 23 and 24 a dotted line is shown to represent the original location of the catheter sheath, and the dotted line is not meant to represent a calibration mark. A calibration mark is optional.)

While discussed above using a surface of a catheter sheath as a reference item which is used as a basis for calibration, other reference items are suitable. For example, any item that can be depicted such that its expected location and actual location can be compared in a display of an imaging system may be used. In some embodiments, a fiducial marker or calibration bar is introduced into the imaging target having a known dimension (e.g., 1 nm, 1 mm, 1 cm). The system operates to display a scale or a grid based on an expected appearance of the known dimension. The user then gives input indicating a point in the display near the reference item and the system also detects a location of the reference item in an area around the indicated point. Based on the expected and actual locations or dimensions of the reference item, a calibration value is calculated and a calibrated image is provided. User input, displays, and methods of receiving user input and performing calculations may be provided by one or more computers.

In certain embodiments, display 237 is rendered within a computer operating system environment, such as Windows, Mac OS, or Linux or within a display or GUI of a specialized system. Display 237 can include any standard controls associated with a display (e.g., within a windowing environment) including minimize and close buttons, scroll bars, menus, and window resizing controls. Elements of display 237 can be provided by an operating system, windows environment, application programing interface (API), web browser, program, or combination thereof (for example, in some embodiments a computer includes an operating system in which an independent program such as a web browser runs and the independent program supplies one or more of an API to render elements of a GUI). Display 237 can further include any controls or information related to viewing images (e.g., zoom, color controls, brightness/contrast) or handling files comprising three-dimensional image data (e.g., open, save, close, select, cut, delete, etc.). Further, display 237 can include controls (e.g., buttons, sliders, tabs, switches) related to operating a three dimensional image capture system (e.g., go, stop, pause, power up, power down).

In certain embodiments, display 237 includes controls related to three dimensional imaging systems that are operable with different imaging modalities. For example, display 237 may include start, stop, zoom, save, etc., buttons, and be rendered by a computer program that interoperates with OCT or IVUS modalities. Thus display 237 can display an image derived from a three-dimensional data set with or without regard to the imaging mode of the system.

Figure 25:
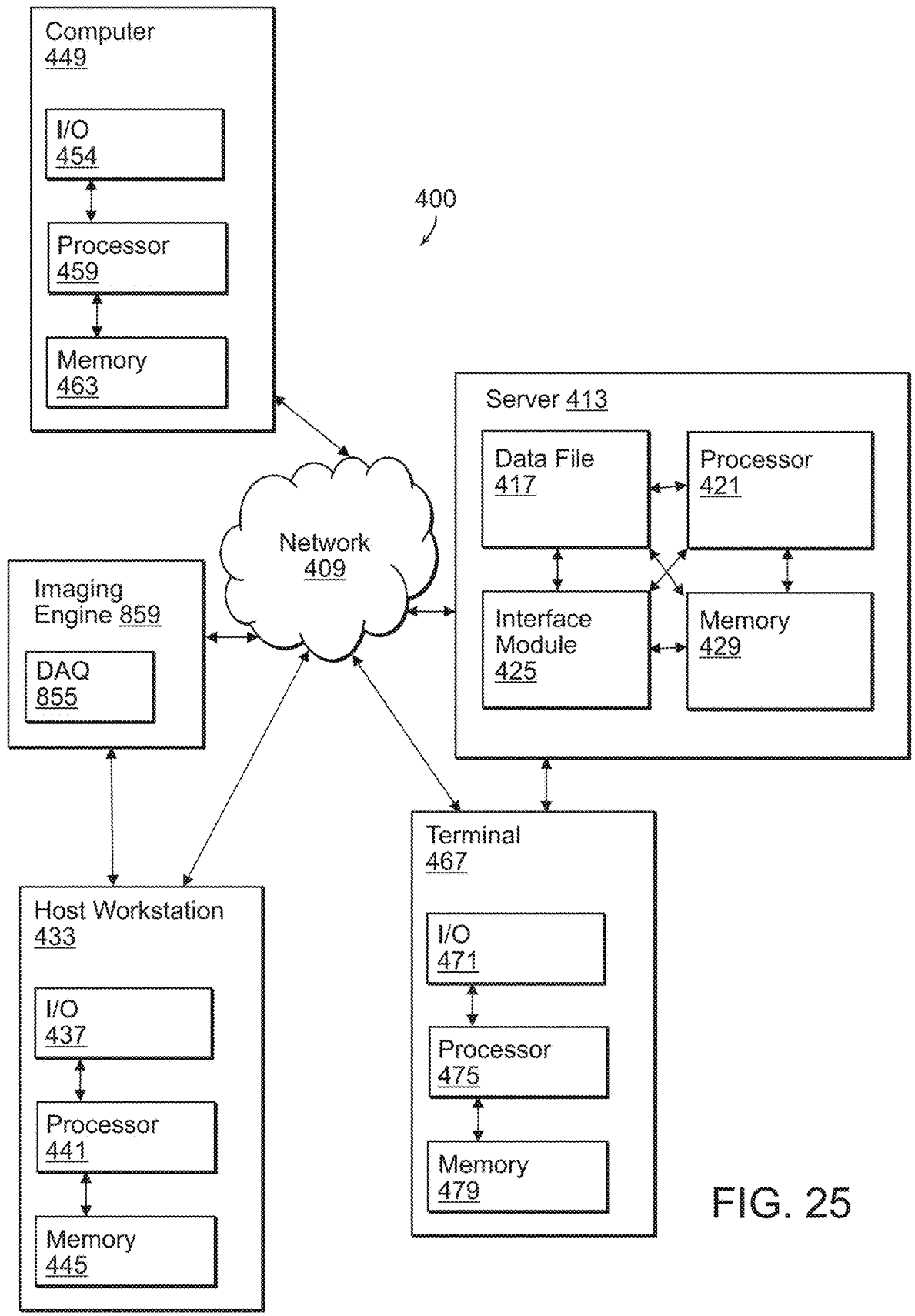
FIG. 25 illustrates components of a system according to certain embodiments of the invention.

FIG. 25 diagrams an exemplary system 400. As shown in FIG. 25, imaging engine 859 communicates with host workstation 433 as well as optionally server 413 over network 409. In some embodiments, an operator uses host workstation 433, computer 449, or terminal 467 to control system 400 or to receive images. An image may be displayed using an I/O 454, 437, or 471, which may include a monitor. Any I/O may include a monitor, keyboard, mouse or touchscreen to communicate with any of processor 421, 459, 441, or 475, for example, to cause data to be stored in any tangible, nontransitory memory 463, 445, 479, or 429. Server 413 generally includes an interface module 425 to communicate over network 409 or write data to data file 417. Input from a user is received by a processor in an electronic device such as, for example, host workstation 433, server 413, or computer 449. Methods of the invention can be performed using software, hardware, firmware, hardwiring, or combinations of any of these. Features implementing functions can also be physically located at various positions, including being distributed such that portions of functions are implemented at different physical locations (e.g., imaging apparatus in one room and host workstation in another, or in separate buildings, for example, with wireless or wired connections). In certain embodiments, host workstation 433 and imaging engine 855 are included in a bedside console unit to operate system 400.

A computer generally includes a processor for executing instructions and one or more memory devices for storing instructions, data, or both. Processors suitable for the execution of methods and operations described herein include, by way of example, both general and special purpose microprocessors (e.g., an Intel chip, an AMD chip, an FPGA). Generally, a processor will receive instructions or data from read-only memory, random access memory, or both. Generally, a computer will also include, or be operatively coupled, one or more mass storage devices for storing data that represent target such as bodily tissue. Any suitable computer-readable storage device may be used such as, for example, solid-state, magnetic, magneto-optical disks, or optical disks. Information carriers suitable for embodying computer program instructions and data include all forms of non-volatile memory, particularly tangible, non-transitory memory including by way of example semiconductor memory devices, (e.g., EPROM, EEPROM, NAND-based flash memory, solid state drive (SSD), and other flash memory devices); magnetic disks, (e.g., internal hard disks or removable disks); magneto-optical disks; and optical disks (e.g., CD and DVD disks).

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

The invention claimed is:

1. A method of calibrating an imaging system, the method comprising:
    obtaining, by an imaging device of the imaging system, an image showing a target and a reference item, wherein the reference item comprises a structure of the imaging device disposed within the target;
    displaying the image showing the target and the reference item;
    receiving a user input indicating a point on or near the reference item, wherein the reference item and the point are located within the target on the image;
    detecting, via a morphological imaging processing operation, a portion of the reference item within an area around the indicated point, wherein the morphological imaging processing operation is selected from the group consisting of erosion, dilation, opening, and closing, and a combination thereof;
    in response to detecting the portion of the reference item:
        detecting, via the morphological imaging processing operation, a remaining portion of the reference item using an expanded area around the indicated point; and determining a radial distance of the reference item from the imaging device;

calculating a calibration value based on the radial distance of the reference item; and providing, based on the calibration value, a calibrated image of the target at a known scale.

2. The method of claim 1, wherein the imaging system is an optical coherence tomography system, and wherein providing the calibrated image comprises changing a reference path length of the imaging system to match a sample path length according to the calibration value.

3. The method of claim 1, wherein the reference item comprises a catheter sheath.

4. The method of claim 1, further comprising moving a component of the imaging system based on the calculated calibration value and performing a scan to provide the calibrated image.

5. The method of claim 1, further comprising digitally transforming image data to provide the calibrated image.

6. The method of claim 1, wherein the user input is a single mouse click or a single touch of a touchscreen.

7. The method of claim 1, wherein the area comprises a predetermined polygon or circle around the indicated point.

8. The method of claim 7, wherein the area is within the expanded area.

9. The method of claim 1, wherein the calibration value represents a z-offset associated with an interferometric device.

10. The method of claim 1, wherein the imaging device comprises a transducer.

11. An imaging system comprising:
a processor and a computer-readable storage medium having instructions therein which, when executed by the processor, cause the system to:
receive, from an imaging device of the imaging system, an image showing a target and a reference item, wherein the reference item comprises a structure of the imaging device disposed within the target;
display the image showing the target and the reference item;
receive a user input indicating a point on or near the reference item, wherein the reference item and the point are located within the target on the image;
detect, via a morphological image processing operation, a portion of the reference item within an area around the indicated point, wherein the morphological imaging processing operation is selected from the group consisting of erosion, dilation, opening, and closing, and a combination thereof;
in response to detecting the portion of the reference item:
detect, via the morphological imaging processing operation, a remaining portion of the reference item using an expanded area around the indicated point; and
determine a radial distance of the reference item from the imaging device;
calculate a calibration value based on the radial distance of the reference item; and
provide, based on the calibration value, a calibrated image of the target at a known scale.

12. The system of claim 11,
wherein the imaging system is an optical coherence tomography system, and
wherein the computer-readable storage medium further has instructions therein which, when executed by the processor, cause the system to change a reference path length of the imaging system to match a sample path length according to the calibration value.

13. The system of claim 11, wherein the reference item comprises a catheter sheath.

14. The system of claim 12, further comprising a motor to move a component of the imaging system based on the calculated calibration value, wherein moving the component alters the reference path length.

15. The system of claim 11, further wherein the system further digitally transforms image data to provide the calibrated image.

16. The system of claim 11, wherein the user input is a single mouse click or a single touch of a touchscreen.

17. The system of claim 11, wherein the area comprises a predetermined polygon or circle around the indicated point.

18. The system of claim 11, wherein the computer-readable storage medium has stored therein an expected location of the reference item.

19. The system of claim 11, wherein the calibration value represents a z-offset associated with an interferometric device.

20. The system of claim 11, further comprising the imaging device, wherein the imaging device comprises a transducer.

* * * * *